US005670356A

United States Patent [19]

Sherf et al.

[11] Patent Number: 5,670,356
[45] Date of Patent: Sep. 23, 1997

[54] MODIFIED LUCIFERASE

[75] Inventors: Bruce A. Sherf, Waunakee; Keith V. Wood, Madison, both of Wis.

[73] Assignee: Promega Corporation, Madison, Wis.

[21] Appl. No.: 354,240

[22] Filed: Dec. 12, 1994

[51] Int. Cl.$^6$ .............. C12N 9/02; C12N 15/53; C12N 5/10; C07H 21/04
[52] U.S. Cl. .............. 435/189; 435/172.1; 435/172.3; 435/240.2; 536/23.2
[58] Field of Search .............. 435/172.3, 172.1, 435/69.7, 240.2, 189; 536/23.2

[56] References Cited

U.S. PATENT DOCUMENTS

| | | |
|---|---|---|
| 4,412,001 | 10/1983 | Baldwin et al. |
| 4,503,142 | 3/1985 | Berman et al. ............ 435/6 |
| 4,581,335 | 4/1986 | Baldwin et al. |
| 4,968,613 | 11/1990 | Masuda et al. |
| 5,182,202 | 1/1993 | Kajiyama et al. |
| 5,196,524 | 3/1993 | Gustafson et al. |
| 5,219,737 | 6/1993 | Kajiyama et al. |
| 5,221,623 | 6/1993 | Legocki et al. |
| 5,229,285 | 7/1993 | Kajiyama et al. |

FOREIGN PATENT DOCUMENTS

| | | |
|---|---|---|
| A1-0-353-464 | 2/1990 | European Pat. Off. |
| A1-0-364-707 | 4/1990 | European Pat. Off. |
| PCT/JP89/00811 | 2/1990 | WIPO |
| PCT/US91/01614 | 9/1992 | WIPO |

OTHER PUBLICATIONS

Bonin et al (1994) "*Photinus pyralis* luciferase" *Gene* 141:75–77.
Fuerst et al. (1989) "Structure & stability of mRNA . . ." *J. Mol. Biol.* 206:333–348.
Fleer et al. (1991) "High–level secretion of correctly processed . . ." *Gene* 107:285–295.
Sala–Newby et al. (1994) "Stepwise removal of the C–terminal 12 amino acids . . . " *Biochim Biophys Acta* 1206:155–160.
Salsa–Newby et al. (1992) "Engineeering firefly luciferase . . . " *FEBS Lett.* 307(2):241–244.
Sala–Newby et al. (1992) "Expression of recombinant firefly luciferase . . . " *Biochem Soc. Transact.* 20:143S.
Bronstein et al (1994) Cal. Biochem: 219, 169–181.
Bachmair et al (1986) Science: 234, 179–186.
de Wet et al (1985) PNAS:82,7870–7873.
de Wet et al (1987) Molecular Cell Biology:7, 725–737.
Faisst, S. & Meyer, S. (1992) Nucleic Acid Res: 20, 3–26.
Gould, S.J. et al (1990) J Cell Biology 110: 27–34.
Gould, S.J. et al (1989) J Cell Biology 108: 1657–1664.
Keller, G.A. et al (1987) J Cell Biology 84: 3264–3268.
Lewis, M.K. & Thompson, D.V. (1990) Nucleic Acid Res 18: 3439–3443.
Lorenz, W.W. (1991) PNAS 88: 4438–4442.
Sommer, J.M. et al. (1992) Molecular Biology 3: 749–759.
Wada, K. et al. (1992) Nucleic Acid Res 20: 2111–2118.
Wood, K.V. & DeLuca, M. (1987) Anal Biochem 161: 501–507.
Gould, Stephen J. and Suresh Subramani, Firefly Luciferase as a Tool in Molecular and Cell Biology, *Analytical Biochemistry* (1988), 175, 5–13.
Pinto, Moise; Morange, Michel and Bensaude, Olivier, Denaturation of Proteins during Heat Shock–In vivo Recovery of Solubility and Activity of reporter Enzymes, *The Journal of Biological Chemistry* (1991), vol. 266, No. 21, Issue of Jul. 25, pp. 13941–13946.

*Primary Examiner*—Robert A. Wax
*Assistant Examiner*—Kawai Lau
*Attorney, Agent, or Firm*—DeWitt Ross & Stevens SC

[57] ABSTRACT

A modified form of beetle luciferase, which has been engineered for improved genetic reporting, is disclosed. The modified form contains one or more new features. Chief among these is removal of the peroxisomal translocation sequence to yield a cytoplasmic form of the enzyme. Other changes include removal of potentially interfering restriction sites and genetic regulatory sites from the gene, improvement of the codon usage for mammalian cells. The modified luciferase reporter enzyme is also devoid of potential N-glycosylation targets to minimize post-translational modification and remains in the cytoplasm of host cells to optimize substrate availability.

17 Claims, 6 Drawing Sheets

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 1650 base pairs
        ( B ) TYPE: nucleic acid
        ( C ) STRANDEDNESS: single
        ( D ) TOPOLOGY: linear ( i i ) MOLECULE TYPE: cDNA ( v ) FRAGMENT TYPE: C-terminal ( v i ) ORIGINAL SOURCE:
        ( A ) ORGANISM: Photinus pyralis ( i x ) FEATURE:
        ( A ) NAME/KEY: CDS
        ( B ) LOCATION: 1..1649

( x i ) SEQUENCE DESCRIPTION: SEQ ID NO:1:

```
ATG GAA GAC GCC AAA AAC ATA AAG AAA GGC CCG GCG CCA TTC TAT CCT      48
Met Glu Asp Ala Lys Asn Ile Lys Lys Gly Pro Ala Pro Phe Tyr Pro
 1               5                  10                  15

CTA GAG GAT GGA ACC GCT GGA GAG CAA CTG CAT AAG GCT ATG AAG AGA      96
Leu Glu Asp Gly Thr Ala Gly Glu Gln Leu His Lys Ala Met Lys Arg
             20                  25                  30

TAC GCC CTG GTT CCT GGA ACA ATT GCT TTT ACA GAT GCA CAT ATC GAG     144
Tyr Ala Leu Val Pro Gly Thr Ile Ala Phe Thr Asp Ala His Ile Glu
         35                  40                  45

GTG AAC ATC ACG TAC GCG GAA TAC TTC GAA ATG TCC GTT CGG TTG GCA     192
Val Asn Ile Thr Tyr Ala Glu Tyr Phe Glu Met Ser Val Arg Leu Ala
     50                  55                  60

GAA GCT ATG AAA CGA TAT GGG CTG AAT ACA AAT CAC AGA ATC GTC GTA     240
Glu Ala Met Lys Arg Tyr Gly Leu Asn Thr Asn His Arg Ile Val Val
 65                  70                  75                  80

TGC AGT GAA AAC TCT CTT CAA TTC TTT ATG CCG GTG TTG GGC GCG TTA     288
Cys Ser Glu Asn Ser Leu Gln Phe Phe Met Pro Val Leu Gly Ala Leu
                 85                  90                  95

TTT ATC GGA GTT GCA GTT GCG CCC GCG AAC GAC ATT TAT AAT GAA CGT     336
```

-continued

| | | | | | | | | | | | | | | | | |
|---|---|---|---|---|---|---|---|---|---|---|---|---|---|---|---|---|
| Phe | Ile | Gly | Val<br>100 | Ala | Val | Ala | Pro | Ala<br>105 | Asn | Asp | Ile | Tyr | Asn<br>110 | Glu | Arg | |
| GAA<br>Glu | TTG<br>Leu | CTC<br>Leu<br>115 | AAC<br>Asn | AGT<br>Ser | ATG<br>Met | AAC<br>Asn | ATT<br>Ile<br>120 | TCG<br>Ser | CAG<br>Gln | CCT<br>Pro | ACC<br>Thr | GTA<br>Val<br>125 | GTG<br>Val | TTT<br>Phe | GTT<br>Val | 384 |
| TCC<br>Ser | AAA<br>Lys<br>130 | AAG<br>Lys | GGG<br>Gly | TTG<br>Leu | CAA<br>Gln<br>135 | AAA<br>Lys | ATT<br>Ile | TTG<br>Leu | AAC<br>Asn | GTG<br>Val<br>140 | CAA<br>Gln | AAA<br>Lys | AAA<br>Lys | TTA<br>Leu | CCA<br>Pro | 432 |
| ATA<br>Ile<br>145 | ATC<br>Ile | CAG<br>Gln | AAA<br>Lys | ATT<br>Ile<br>150 | ATT<br>Ile | ATC<br>Ile | ATG<br>Met | GAT<br>Asp | TCT<br>Ser<br>155 | AAA<br>Lys | ACG<br>Thr | GAT<br>Asp | TAC<br>Tyr | CAG<br>Gln<br>160 | GGA<br>Gly | 480 |
| TTT<br>Phe | CAG<br>Gln | TCG<br>Ser | ATG<br>Met | TAC<br>Tyr<br>165 | ACG<br>Thr | TTC<br>Phe | GTC<br>Val | ACA<br>Thr | TCT<br>Ser<br>170 | CAT<br>His | CTA<br>Leu | CCT<br>Pro | CCC<br>Pro | GGT<br>Gly<br>175 | TTT<br>Phe | 528 |
| AAT<br>Asn | GAA<br>Glu | TAC<br>Tyr | GAT<br>Asp<br>180 | TTT<br>Phe | GTA<br>Val | CCA<br>Pro | GAG<br>Glu | TCC<br>Ser<br>185 | TTT<br>Phe | GAT<br>Asp | CGT<br>Arg | GAC<br>Asp | AAA<br>Lys<br>190 | ACA<br>Thr | ATT<br>Ile | 576 |
| GCA<br>Ala | CTG<br>Leu | ATA<br>Ile | ATG<br>Met<br>195 | AAT<br>Asn | TCC<br>Ser | TCT<br>Ser | GGA<br>Gly | TCT<br>Ser<br>200 | ACT<br>Thr | GGG<br>Gly | TTA<br>Leu | CCT<br>Pro | AAG<br>Lys<br>205 | GGT<br>Gly | GTG<br>Val | 624 |
| GCC<br>Ala | CTT<br>Leu<br>210 | CCG<br>Pro | CAT<br>His | AGA<br>Arg | ACT<br>Thr | GCC<br>Ala<br>215 | TGC<br>Cys | GTC<br>Val | AGA<br>Arg | TTC<br>Phe | TCG<br>Ser<br>220 | CAT<br>His | GCC<br>Ala | AGA<br>Arg | GAT<br>Asp | 672 |
| CCT<br>Pro<br>225 | ATT<br>Ile | TTT<br>Phe | GGC<br>Gly | AAT<br>Asn | CAA<br>Gln<br>230 | ATC<br>Ile | ATT<br>Ile | CCG<br>Pro | GAT<br>Asp | ACT<br>Thr<br>235 | GCG<br>Ala | ATT<br>Ile | TTA<br>Leu | AGT<br>Ser | GTT<br>Val<br>240 | 720 |
| GTT<br>Val | CCA<br>Pro | TTC<br>Phe | CAT<br>His | CAC<br>His<br>245 | GGT<br>Gly | TTT<br>Phe | GGA<br>Gly | ATG<br>Met | TTT<br>Phe<br>250 | ACT<br>Thr | ACA<br>Thr | CTC<br>Leu | GGA<br>Gly | TAT<br>Tyr<br>255 | TTG<br>Leu | 768 |
| ATA<br>Ile | TGT<br>Cys | GGA<br>Gly | TTT<br>Phe<br>260 | CGA<br>Arg | GTC<br>Val | GTC<br>Val | TTA<br>Leu | ATG<br>Met<br>265 | TAT<br>Tyr | AGA<br>Arg | TTT<br>Phe | GAA<br>Glu | GAA<br>Glu<br>270 | GAG<br>Glu | CTG<br>Leu | 816 |
| TTT<br>Phe | TTA<br>Leu<br>275 | CGA<br>Arg | TCC<br>Ser | CTT<br>Leu | CAG<br>Gln | GAT<br>Asp<br>280 | TAC<br>Tyr | AAA<br>Lys | ATT<br>Ile | CAA<br>Gln | AGT<br>Ser<br>285 | GCG<br>Ala | TTG<br>Leu | CTA<br>Leu | GTA<br>Val | 864 |
| CCA<br>Pro | ACC<br>Thr<br>290 | CTA<br>Leu | TTT<br>Phe | TCA<br>Ser | TTC<br>Phe | TTC<br>Phe<br>295 | GCC<br>Ala | AAA<br>Lys | AGC<br>Ser | ACT<br>Thr | CTG<br>Leu<br>300 | ATT<br>Ile | GAC<br>Asp | AAA<br>Lys | TAC<br>Tyr | 912 |
| GAT<br>Asp<br>305 | TTA<br>Leu | TCT<br>Ser | AAT<br>Asn | TTA<br>Leu | CAC<br>His<br>310 | GAA<br>Glu | ATT<br>Ile | GCT<br>Ala | TCT<br>Ser | GGG<br>Gly<br>315 | GGC<br>Gly | GCA<br>Ala | CCT<br>Pro | CTT<br>Leu | TCG<br>Ser<br>320 | 960 |
| AAA<br>Lys | GAA<br>Glu | GTC<br>Val | GGG<br>Gly | GAA<br>Glu<br>325 | GCG<br>Ala | GTT<br>Val | GCA<br>Ala | AAA<br>Lys | CGC<br>Arg<br>330 | TTC<br>Phe | CAT<br>His | CTT<br>Leu | CCA<br>Pro | GGG<br>Gly<br>335 | ATA<br>Ile | 1008 |
| CGA<br>Arg | CAA<br>Gln | GGA<br>Gly | TAT<br>Tyr<br>340 | GGG<br>Gly | CTC<br>Leu | ACT<br>Thr | GAG<br>Glu | ACT<br>Thr<br>345 | ACA<br>Thr | TCA<br>Ser | GCT<br>Ala | ATT<br>Ile | CTG<br>Leu<br>350 | ATT<br>Ile | ACA<br>Thr | 1056 |
| CCC<br>Pro | GAG<br>Glu | GGG<br>Gly<br>355 | GAT<br>Asp | GAT<br>Asp | AAA<br>Lys | CCG<br>Pro | GGC<br>Gly<br>360 | GCG<br>Ala | GTC<br>Val | GGT<br>Gly | AAA<br>Lys | GTT<br>Val<br>365 | GTT<br>Val | CCA<br>Pro | TTT<br>Phe | 1104 |
| TTT<br>Phe | GAA<br>Glu<br>370 | GCG<br>Ala | AAG<br>Lys | GTT<br>Val | GTG<br>Val | GAT<br>Asp<br>375 | CTG<br>Leu | GAT<br>Asp | ACC<br>Thr | GGG<br>Gly | AAA<br>Lys<br>380 | ACG<br>Thr | CTG<br>Leu | GGC<br>Gly | GTT<br>Val | 1152 |
| AAT<br>Asn | CAG<br>Gln<br>385 | AGA<br>Arg | GGC<br>Gly | GAA<br>Glu | TTA<br>Leu | TGT<br>Cys<br>390 | GTC<br>Val | AGA<br>Arg | GGA<br>Gly | CCT<br>Pro | ATG<br>Met<br>395 | ATT<br>Ile | ATG<br>Met | TCC<br>Ser | GGT<br>Gly<br>400 | 1200 |
| TAT<br>Tyr | GTA<br>Val | AAC<br>Asn | AAT<br>Asn | CCG<br>Pro<br>405 | GAA<br>Glu | GCG<br>Ala | ACC<br>Thr | AAC<br>Asn | GCC<br>Ala<br>410 | TTG<br>Leu | ATT<br>Ile | GAC<br>Asp | AAG<br>Lys | GAT<br>Asp<br>415 | GGA<br>Gly | 1248 |
| TGG<br>Trp | CTA<br>Leu | CAT<br>His | TCT<br>Ser | GGA<br>Gly | GAC<br>Asp | ATA<br>Ile | GCT<br>Ala | TAC<br>Tyr | TGG<br>Trp | GAC<br>Asp | GAA<br>Glu | GAC<br>Asp | GAA<br>Glu | CAC<br>His | TTC<br>Phe | 1296 |

-continued

| | | | | | | | | | | | | | | | |
|---|---|---|---|---|---|---|---|---|---|---|---|---|---|---|---|
| Trp | Leu | His | Ser<br>420 | Gly | Asp | Ile | Ala | Tyr<br>425 | Trp | Asp | Glu | Asp<br>430 | Glu | His | Phe |

| TTC | ATA | GTT | GAC | CGC | TTG | AAG | TCT | TTA | ATT | AAA | TAC | AAA | GGA | TAT | CAG | 1344 |
|---|---|---|---|---|---|---|---|---|---|---|---|---|---|---|---|---|
| Phe | Ile | Val<br>435 | Asp | Arg | Leu | Lys | Ser<br>440 | Leu | Ile | Lys | Tyr | Lys<br>445 | Gly | Tyr | Gln | |

| GTG | GCC | CCC | GCT | GAA | TTG | GAA | TCG | ATA | TTG | TTA | CAA | CAC | CCC | AAC | ATC | 1392 |
|---|---|---|---|---|---|---|---|---|---|---|---|---|---|---|---|---|
| Val | Ala<br>450 | Pro | Ala | Glu | Leu | Glu<br>455 | Ser | Ile | Leu | Leu | Gln<br>460 | His | Pro | Asn | Ile | |

| TTC | GAC | GCG | GGC | GTG | GCA | GGT | CTT | CCC | GAC | GAT | GAC | GCC | GGT | GAA | CTT | 1440 |
|---|---|---|---|---|---|---|---|---|---|---|---|---|---|---|---|---|
| Phe<br>465 | Asp | Ala | Gly | Val<br>470 | Ala | Gly | Leu | Pro | Asp<br>475 | Asp | Asp | Ala | Gly | Glu | Leu<br>480 | |

| CCC | GCC | GCC | GTT | GTT | GTT | TTG | GAG | CAC | GGA | AAG | ACG | ATG | ACG | GAA | AAA | 1488 |
|---|---|---|---|---|---|---|---|---|---|---|---|---|---|---|---|---|
| Pro | Ala | Ala | Val<br>485 | Val | Leu | Glu | His | Gly<br>490 | Lys | Thr | Met | Thr | Glu<br>495 | Lys | | |

| GAG | ATC | GTG | GAT | TAC | GTC | GCC | AGT | CAA | GTA | ACA | ACC | GCG | AAA | AAG | TTG | 1536 |
|---|---|---|---|---|---|---|---|---|---|---|---|---|---|---|---|---|
| Glu | Ile | Val | Asp<br>500 | Tyr | Val | Ala | Ser | Gln<br>505 | Val | Thr | Thr | Ala | Lys<br>510 | Lys | Leu | |

| CGC | GGA | GGA | GTT | GTG | TTT | GTG | GAC | GAA | GTA | CCG | AAA | GGT | CTT | ACC | GGA | 1584 |
|---|---|---|---|---|---|---|---|---|---|---|---|---|---|---|---|---|
| Arg | Gly | Gly<br>515 | Val | Val | Phe | Val | Asp<br>520 | Glu | Val | Pro | Lys | Gly<br>525 | Leu | Thr | Gly | |

| AAA | CTC | GAC | GCA | AGA | AAA | ATC | AGA | GAG | ATC | CTC | ATA | AAG | GCC | AAG | AAG | 1632 |
|---|---|---|---|---|---|---|---|---|---|---|---|---|---|---|---|---|
| Lys | Leu | Asp<br>530 | Ala | Arg | Lys | Ile<br>535 | Arg | Glu | Ile | Leu | Ile<br>540 | Lys | Ala | Lys | Lys | |

| GGC | GGA | AAG | TCC | AAA | TT G | 1650 |
|---|---|---|---|---|---|---|
| Gly | Gly | Lys | Ser | Lys<br>545 | | |

( 2 ) INFORMATION FOR SEQ ID NO:2:

( i ) SEQUENCE CHARACTERISTICS:
        ( A ) LENGTH: 549 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met<br>1 | Glu | Asp | Ala | Lys<br>5 | Asn | Ile | Lys | Lys | Gly<br>10 | Pro | Ala | Pro | Phe | Tyr<br>15 | Pro |
| Leu | Glu | Asp | Gly<br>20 | Thr | Ala | Gly | Glu | Gln<br>25 | Leu | His | Lys | Ala | Met<br>30 | Lys | Arg |
| Tyr | Ala | Leu<br>35 | Val | Pro | Gly | Thr | Ile<br>40 | Ala | Phe | Thr | Asp | Ala<br>45 | His | Ile | Glu |
| Val | Asn | Ile<br>50 | Thr | Tyr | Ala | Glu | Tyr<br>55 | Phe | Glu | Met | Ser | Val<br>60 | Arg | Leu | Ala |
| Glu<br>65 | Ala | Met | Lys | Arg | Tyr<br>70 | Gly | Leu | Asn | Thr | Asn<br>75 | His | Arg | Ile | Val | Val<br>80 |
| Cys | Ser | Glu | Asn | Ser<br>85 | Leu | Gln | Phe | Phe | Met<br>90 | Pro | Val | Leu | Gly | Ala<br>95 | Leu |
| Phe | Ile | Gly | Val<br>100 | Ala | Val | Ala | Pro | Ala<br>105 | Asn | Asp | Ile | Tyr | Asn<br>110 | Glu | Arg |
| Glu | Leu | Leu | Asn<br>115 | Ser | Met | Asn | Ile | Ser<br>120 | Gln | Pro | Thr | Val | Val<br>125 | Phe | Val |
| Ser | Lys | Lys<br>130 | Gly | Leu | Gln | Lys | Ile<br>135 | Leu | Asn | Val | Gln | Lys<br>140 | Lys | Leu | Pro |
| Ile<br>145 | Ile | Gln | Lys | Ile | Ile<br>150 | Ile | Met | Asp | Ser | Lys<br>155 | Thr | Asp | Tyr | Gln | Gly<br>160 |
| Phe | Gln | Ser | Met | Tyr<br>165 | Thr | Phe | Val | Thr | Ser<br>170 | His | Leu | Pro | Pro | Gly<br>175 | Phe |

| Asn | Glu | Tyr | Asp | Phe | Val | Pro | Glu | Ser | Phe | Asp | Arg | Asp | Lys | Thr | Ile |
| --- | --- | --- | --- | --- | --- | --- | --- | --- | --- | --- | --- | --- | --- | --- | --- |
| | | | 180 | | | | 185 | | | | | 190 | | | |
| Ala | Leu | Ile | Met | Asn | Ser | Ser | Ser | Thr | Gly | Leu | Pro | Lys | Gly | Val | |
| | | 195 | | | | 200 | | | | | 205 | | | | |
| Ala | Leu | Pro | His | Arg | Thr | Ala | Cys | Val | Arg | Phe | Ser | His | Ala | Arg | Asp |
| 210 | | | | | 215 | | | | | | 220 | | | | |
| Pro | Ile | Phe | Gly | Asn | Gln | Ile | Ile | Pro | Asp | Thr | Ala | Ile | Leu | Ser | Val |
| 225 | | | | 230 | | | | | 235 | | | | | | 240 |
| Val | Pro | Phe | His | His | Gly | Phe | Gly | Met | Phe | Thr | Thr | Leu | Gly | Tyr | Leu |
| | | | | 245 | | | | | 250 | | | | | 255 | |
| Ile | Cys | Gly | Phe | Arg | Val | Val | Leu | Met | Tyr | Arg | Phe | Glu | Glu | Leu | |
| | | | 260 | | | | | 265 | | | | | 270 | | |
| Phe | Leu | Arg | Ser | Leu | Gln | Asp | Tyr | Lys | Ile | Gln | Ser | Ala | Leu | Leu | Val |
| | | 275 | | | | | 280 | | | | | 285 | | | |
| Pro | Thr | Leu | Phe | Ser | Phe | Phe | Ala | Lys | Ser | Thr | Leu | Ile | Asp | Lys | Tyr |
| | 290 | | | | | 295 | | | | | 300 | | | | |
| Asp | Leu | Ser | Asn | Leu | His | Glu | Ile | Ala | Ser | Gly | Gly | Ala | Pro | Leu | Ser |
| 305 | | | | | 310 | | | | | 315 | | | | | 320 |
| Lys | Glu | Val | Gly | Glu | Ala | Val | Ala | Lys | Arg | Phe | His | Leu | Pro | Gly | Ile |
| | | | | 325 | | | | | 330 | | | | | 335 | |
| Arg | Gln | Gly | Tyr | Gly | Leu | Thr | Glu | Thr | Thr | Ser | Ala | Ile | Leu | Ile | Thr |
| | | | 340 | | | | | 345 | | | | | 350 | | |
| Pro | Glu | Gly | Asp | Asp | Lys | Pro | Gly | Ala | Val | Gly | Lys | Val | Val | Pro | Phe |
| | | 355 | | | | | 360 | | | | | 365 | | | |
| Phe | Glu | Ala | Lys | Val | Val | Asp | Leu | Asp | Thr | Gly | Lys | Thr | Leu | Gly | Val |
| | 370 | | | | | 375 | | | | | 380 | | | | |
| Asn | Gln | Arg | Gly | Glu | Leu | Cys | Val | Arg | Gly | Pro | Met | Ile | Met | Ser | Gly |
| 385 | | | | | 390 | | | | | 395 | | | | | 400 |
| Tyr | Val | Asn | Asn | Pro | Glu | Ala | Thr | Asn | Ala | Leu | Ile | Asp | Lys | Asp | Gly |
| | | | | 405 | | | | | 410 | | | | | 415 | |
| Trp | Leu | His | Ser | Gly | Asp | Ile | Ala | Tyr | Trp | Asp | Glu | Asp | Glu | His | Phe |
| | | | 420 | | | | | 425 | | | | | 430 | | |
| Phe | Ile | Val | Asp | Arg | Leu | Lys | Ser | Leu | Ile | Lys | Tyr | Lys | Gly | Tyr | Gln |
| | | 435 | | | | | 440 | | | | | 445 | | | |
| Val | Ala | Pro | Ala | Glu | Leu | Glu | Ser | Ile | Leu | Leu | Gln | His | Pro | Asn | Ile |
| | 450 | | | | | 455 | | | | | 460 | | | | |
| Phe | Asp | Ala | Gly | Val | Ala | Gly | Leu | Pro | Asp | Asp | Asp | Ala | Gly | Glu | Leu |
| 465 | | | | | 470 | | | | | 475 | | | | | 480 |
| Pro | Ala | Ala | Val | Val | Val | Leu | Glu | His | Gly | Lys | Thr | Met | Thr | Glu | Lys |
| | | | | 485 | | | | | 490 | | | | | 495 | |
| Glu | Ile | Val | Asp | Tyr | Val | Ala | Ser | Gln | Val | Thr | Thr | Ala | Lys | Lys | Leu |
| | | | 500 | | | | | 505 | | | | | 510 | | |
| Arg | Gly | Gly | Val | Val | Phe | Val | Asp | Glu | Val | Pro | Lys | Gly | Leu | Thr | Gly |
| | | 515 | | | | | 520 | | | | | 525 | | | |
| Lys | Leu | Asp | Ala | Arg | Lys | Ile | Arg | Glu | Ile | Leu | Ile | Lys | Ala | Lys | Lys |
| | 530 | | | | | 535 | | | | | 540 | | | | |
| Gly | Gly | Lys | Ser | Lys | | | | | | | | | | | |
| 545 | | | | | | | | | | | | | | | |

(2) INFORMATION FOR SEQ ID NO:3:

(i) SEQUENCE CHARACTERISTICS:
        (A) LENGTH: 1650 base pairs
        (B) TYPE: nucleic acid
        (C) STRANDEDNESS: single
        (D) TOPOLOGY: linear ( i i ) MOLECULE TYPE: cDNA ( v ) FRAGMENT TYPE: C-terminal ( v i ) ORIGINAL SOURCE:
 ( A ) ORGANISM: Photinus pyralis ( i x ) FEATURE:
 ( A ) NAME/KEY: CDS
 ( B ) LOCATION: 1..1651

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| ATG | GAA | GAC | GCC | AAA | AAC | ATA | AAG | AAA | GGC | CCG | GCG | CCA | TTC | TAT | CCG | 48 |
| Met | Glu | Asp | Ala | Lys | Asn | Ile | Lys | Lys | Gly | Pro | Ala | Pro | Phe | Tyr | Pro | |
| 1 | | | | 5 | | | | | 10 | | | | | 15 | | |
| CTG | GAA | GAT | GGA | ACC | GCT | GGA | GAG | CAA | CTG | CAT | AAG | GCT | ATG | AAG | AGA | 96 |
| Leu | Glu | Asp | Gly | Thr | Ala | Gly | Glu | Gln | Leu | His | Lys | Ala | Met | Lys | Arg | |
| | | | 20 | | | | | 25 | | | | | 30 | | | |
| TAC | GCC | CTG | GTT | CCT | GGA | ACA | ATT | GCT | TTT | ACA | GAT | GCA | CAT | ATC | GAG | 144 |
| Tyr | Ala | Leu | Val | Pro | Gly | Thr | Ile | Ala | Phe | Thr | Asp | Ala | His | Ile | Glu | |
| | | 35 | | | | | 40 | | | | | 45 | | | | |
| GTG | GAC | ATC | ACT | TAC | GCT | GAG | TAC | TTC | GAA | ATG | TCC | GTT | CGG | TTG | GCA | 192 |
| Val | Asp | Ile | Thr | Tyr | Ala | Glu | Tyr | Phe | Glu | Met | Ser | Val | Arg | Leu | Ala | |
| | 50 | | | | | 55 | | | | | 60 | | | | | |
| GAA | GCT | ATG | AAA | CGA | TAT | GGG | CTG | AAT | ACA | AAT | CAC | AGA | ATC | GTC | GTA | 240 |
| Glu | Ala | Met | Lys | Arg | Tyr | Gly | Leu | Asn | Thr | Asn | His | Arg | Ile | Val | Val | |
| 65 | | | | | 70 | | | | | 75 | | | | | 80 | |
| TGC | AGT | GAA | AAC | TCT | CTT | CAA | TTC | TTT | ATG | CCG | GTG | TTG | GGC | GCG | TTA | 288 |
| Cys | Ser | Glu | Asn | Ser | Leu | Gln | Phe | Phe | Met | Pro | Val | Leu | Gly | Ala | Leu | |
| | | | | 85 | | | | | 90 | | | | | 95 | | |
| TTT | ATC | GGA | GTT | GCA | GTT | GCG | CCC | GCG | AAC | GAC | ATT | TAT | AAT | GAA | CGT | 336 |
| Phe | Ile | Gly | Val | Ala | Val | Ala | Pro | Ala | Asn | Asp | Ile | Tyr | Asn | Glu | Arg | |
| | | | 100 | | | | | 105 | | | | | 110 | | | |
| GAA | TTG | CTC | AAC | AGT | ATG | GGC | ATT | TCG | CAG | CCT | ACC | GTG | GTG | TTC | GTT | 384 |
| Glu | Leu | Leu | Asn | Ser | Met | Gly | Ile | Ser | Gln | Pro | Thr | Val | Val | Phe | Val | |
| | | 115 | | | | | 120 | | | | | 125 | | | | |
| TCC | AAA | AAG | GGG | TTG | CAA | AAA | ATT | TTG | AAC | GTG | CAA | AAA | AAG | CTC | CCA | 432 |
| Ser | Lys | Lys | Gly | Leu | Gln | Lys | Ile | Leu | Asn | Val | Gln | Lys | Lys | Leu | Pro | |
| | 130 | | | | | 135 | | | | | 140 | | | | | |
| ATC | ATC | CAA | AAA | ATT | ATT | ATC | ATG | GAT | TCT | AAA | ACG | GAT | TAC | CAG | GGA | 480 |
| Ile | Ile | Gln | Lys | Ile | Ile | Ile | Met | Asp | Ser | Lys | Thr | Asp | Tyr | Gln | Gly | |
| 145 | | | | | 150 | | | | | 155 | | | | | 160 | |
| TTT | CAG | TCG | ATG | TAC | ACG | TTC | GTC | ACA | TCT | CAT | CTA | CCT | CCC | GGT | TTT | 528 |
| Phe | Gln | Ser | Met | Tyr | Thr | Phe | Val | Thr | Ser | His | Leu | Pro | Pro | Gly | Phe | |
| | | | | 165 | | | | | 170 | | | | | 175 | | |
| AAT | GAA | TAC | GAT | TTT | GTG | CCA | GAG | TCC | TTC | GAT | AGG | GAC | AAG | ACA | ATT | 576 |
| Asn | Glu | Tyr | Asp | Phe | Val | Pro | Glu | Ser | Phe | Asp | Arg | Asp | Lys | Thr | Ile | |
| | | | 180 | | | | | 185 | | | | | 190 | | | |
| GCA | CTG | ATC | ATG | AAC | TCC | TCT | GGA | TCT | ACT | GGT | CTG | CCT | AAA | GGT | GTC | 624 |
| Ala | Leu | Ile | Met | Asn | Ser | Ser | Gly | Ser | Thr | Gly | Leu | Pro | Lys | Gly | Val | |
| | | 195 | | | | | 200 | | | | | 205 | | | | |
| GCT | CTG | CCT | CAT | AGA | ACT | GCC | TGC | GTG | AGA | TTC | TCG | CAT | GCC | AGA | GAT | 672 |
| Ala | Leu | Pro | His | Arg | Thr | Ala | Cys | Val | Arg | Phe | Ser | His | Ala | Arg | Asp | |
| | 210 | | | | | 215 | | | | | 220 | | | | | |
| CCT | ATT | TTT | GGC | AAT | CAA | ATC | ATT | CCG | GAT | ACT | GCG | ATT | TTA | AGT | GTT | 720 |
| Pro | Ile | Phe | Gly | Asn | Gln | Ile | Ile | Pro | Asp | Thr | Ala | Ile | Leu | Ser | Val | |
| 225 | | | | | 230 | | | | | 235 | | | | | 240 | |
| GTT | CCA | TTC | CAT | CAC | GGT | TTT | GGA | ATG | TTT | ACT | ACA | CTC | GGA | TAT | TTG | 768 |
| Val | Pro | Phe | His | His | Gly | Phe | Gly | Met | Phe | Thr | Thr | Leu | Gly | Tyr | Leu | |
| | | | | 245 | | | | | 250 | | | | | 255 | | |
| ATA | TGT | GGA | TTT | CGA | GTC | GTC | TTA | ATG | TAT | AGA | TTT | GAA | GAA | GAG | CTG | 816 |
| Ile | Cys | Gly | Phe | Arg | Val | Val | Leu | Met | Tyr | Arg | Phe | Glu | Glu | Glu | Leu | |

|   |   |   |   |   |   |   |   |   |   |   |   |   |   |   |   |
|---|---|---|---|---|---|---|---|---|---|---|---|---|---|---|---|
|   |   |   | 260 |   |   |   | 265 |   |   |   | 270 |   |   |   |   |
| TTT | CTG | AGG | AGC | CTT | CAG | GAT | TAC | AAG | ATT | CAA | AGT | GCG | CTG | CTG | GTG | 864 |
| Phe | Leu | Arg | Ser | Leu | Gln | Asp | Tyr | Lys | Ile | Gln | Ser | Ala | Leu | Leu | Val |   |
|   |   | 275 |   |   |   |   | 280 |   |   |   |   | 285 |   |   |   |   |
| CCA | ACC | CTA | TTC | TCC | TTC | TTC | GCC | AAA | AGC | ACT | CTG | ATT | GAC | AAA | TAC | 912 |
| Pro | Thr | Leu | Phe | Ser | Phe | Phe | Ala | Lys | Ser | Thr | Leu | Ile | Asp | Lys | Tyr |   |
|   |   | 290 |   |   |   |   | 295 |   |   |   |   | 300 |   |   |   |   |
| GAT | TTA | TCT | AAT | TTA | CAC | GAA | ATT | GCT | TCT | GGT | GGC | GCT | CCC | CTC | TCT | 960 |
| Asp | Leu | Ser | Asn | Leu | His | Glu | Ile | Ala | Ser | Gly | Gly | Ala | Pro | Leu | Ser |   |
| 305 |   |   |   |   | 310 |   |   |   |   | 315 |   |   |   |   | 320 |   |
| AAG | GAA | GTC | GGG | GAA | GCG | GTT | GCC | AAG | AGG | TTC | CAT | CTG | CCA | GGT | ATC | 1008 |
| Lys | Glu | Val | Gly | Glu | Ala | Val | Ala | Lys | Arg | Phe | His | Leu | Pro | Gly | Ile |   |
|   |   |   |   | 325 |   |   |   |   | 330 |   |   |   |   | 335 |   |   |
| AGG | CAA | GGA | TAT | GGG | CTC | ACT | GAG | ACT | ACA | TCA | GCT | ATT | CTG | ATT | ACA | 1056 |
| Arg | Gln | Gly | Tyr | Gly | Leu | Thr | Glu | Thr | Thr | Ser | Ala | Ile | Leu | Ile | Thr |   |
|   |   |   |   | 340 |   |   |   |   | 345 |   |   |   |   | 350 |   |   |
| CCC | GAG | GGG | GAT | GAT | AAA | CCG | GGC | GCG | GTC | GGT | AAA | GTT | GTT | CCA | TTT | 1104 |
| Pro | Glu | Gly | Asp | Asp | Lys | Pro | Gly | Ala | Val | Gly | Lys | Val | Val | Pro | Phe |   |
|   |   | 355 |   |   |   |   | 360 |   |   |   |   | 365 |   |   |   |   |
| TTT | GAA | GCG | AAG | GTT | GTG | GAT | CTG | GAT | ACC | GGG | AAA | ACG | CTG | GGC | GTT | 1152 |
| Phe | Glu | Ala | Lys | Val | Val | Asp | Leu | Asp | Thr | Gly | Lys | Thr | Leu | Gly | Val |   |
|   | 370 |   |   |   |   | 375 |   |   |   |   | 380 |   |   |   |   |   |
| AAT | CAA | AGA | GGC | GAA | CTG | TGT | GTG | AGA | GGT | CCT | ATG | ATT | ATG | TCC | GGT | 1200 |
| Asn | Gln | Arg | Gly | Glu | Leu | Cys | Val | Arg | Gly | Pro | Met | Ile | Met | Ser | Gly |   |
| 385 |   |   |   |   | 390 |   |   |   |   | 395 |   |   |   |   | 400 |   |
| TAT | GTA | AAC | AAT | CCG | GAA | GCG | ACC | AAC | GCC | TTG | ATT | GAC | AAG | GAT | GGA | 1248 |
| Tyr | Val | Asn | Asn | Pro | Glu | Ala | Thr | Asn | Ala | Leu | Ile | Asp | Lys | Asp | Gly |   |
|   |   |   |   | 405 |   |   |   |   | 410 |   |   |   |   | 415 |   |   |
| TGG | CTA | CAT | TCT | GGA | GAC | ATA | GCT | TAC | TGG | GAC | GAA | GAC | GAA | CAC | TTC | 1296 |
| Trp | Leu | His | Ser | Gly | Asp | Ile | Ala | Tyr | Trp | Asp | Glu | Asp | Glu | His | Phe |   |
|   |   |   | 420 |   |   |   |   | 425 |   |   |   |   | 430 |   |   |   |
| TTC | ATC | GTT | GAC | CGC | CTG | AAG | TCT | CTG | ATT | AAG | TAC | AAA | GGC | TAT | CAG | 1344 |
| Phe | Ile | Val | Asp | Arg | Leu | Lys | Ser | Leu | Ile | Lys | Tyr | Lys | Gly | Tyr | Gln |   |
|   |   |   | 435 |   |   |   |   | 440 |   |   |   |   | 445 |   |   |   |
| GTG | GCT | CCC | GCT | GAA | TTG | GAA | TCC | ATC | TTG | CTC | CAA | CAC | CCC | AAC | ATC | 1392 |
| Val | Ala | Pro | Ala | Glu | Leu | Glu | Ser | Ile | Leu | Leu | Gln | His | Pro | Asn | Ile |   |
|   | 450 |   |   |   |   | 455 |   |   |   |   | 460 |   |   |   |   |   |
| TTC | GAC | GCA | GGT | GTC | GCA | GGT | CTT | CCC | GAC | GAT | GAC | GCC | GGT | GAA | CTT | 1440 |
| Phe | Asp | Ala | Gly | Val | Ala | Gly | Leu | Pro | Asp | Asp | Asp | Ala | Gly | Glu | Leu |   |
| 465 |   |   |   |   | 470 |   |   |   |   | 475 |   |   |   |   | 480 |   |
| CCC | GCC | GCC | GTT | GTT | GTT | TTG | GAG | CAC | GGA | AAG | ACG | ATG | ACG | GAA | AAA | 1488 |
| Pro | Ala | Ala | Val | Val | Val | Leu | Glu | His | Gly | Lys | Thr | Met | Thr | Glu | Lys |   |
|   |   |   |   | 485 |   |   |   |   | 490 |   |   |   |   | 495 |   |   |
| GAG | ATC | GTG | GAT | TAC | GTC | GCC | AGT | CAA | GTA | ACA | ACC | GCG | AAA | AAG | TTG | 1536 |
| Glu | Ile | Val | Asp | Tyr | Val | Ala | Ser | Gln | Val | Thr | Thr | Ala | Lys | Lys | Leu |   |
|   |   |   |   | 500 |   |   |   |   | 505 |   |   |   |   | 510 |   |   |
| CGC | GGA | GGA | GTT | GTG | TTT | GTG | GAC | GAA | GTA | CCG | AAA | GGT | CTT | ACC | GGA | 1584 |
| Arg | Gly | Gly | Val | Val | Phe | Val | Asp | Glu | Val | Pro | Lys | Gly | Leu | Thr | Gly |   |
|   |   | 515 |   |   |   |   | 520 |   |   |   |   | 525 |   |   |   |   |
| AAA | CTC | GAC | GCA | AGA | AAA | ATC | AGA | GAG | ATC | CTC | ATA | AAG | GCC | AAG | AAG | 1632 |
| Lys | Leu | Asp | Ala | Arg | Lys | Ile | Arg | Glu | Ile | Leu | Ile | Lys | Ala | Lys | Lys |   |
|   | 530 |   |   |   |   | 535 |   |   |   |   | 540 |   |   |   |   |   |
| GGC | GGA | AAG | ATC | GCC | GTG |   |   |   |   |   |   |   |   |   |   | 1650 |
| Gly | Gly | Lys | Ile | Ala | Val |   |   |   |   |   |   |   |   |   |   |   |
| 545 |   |   |   |   | 550 |   |   |   |   |   |   |   |   |   |   |   |

( 2 ) INFORMATION FOR SEQ ID NO:4:

( i ) SEQUENCE CHARACTERISTICS:
        ( A ) LENGTH: 550 amino acids
        ( B ) TYPE: amino acid (D) TOPOLOGY: linear (ii) MOLECULE TYPE: protein (xi) SEQUENCE DESCRIPTION: SEQ ID NO:4:

| Met | Glu | Asp | Ala | Lys | Asn | Ile | Lys | Lys | Gly | Pro | Ala | Pro | Phe | Tyr | Pro |
|---|---|---|---|---|---|---|---|---|---|---|---|---|---|---|---|
| 1 | | | | 5 | | | | | 10 | | | | | 15 | |
| Leu | Glu | Asp | Gly | Thr | Ala | Gly | Glu | Gln | Leu | His | Lys | Ala | Met | Lys | Arg |
| | | | 20 | | | | | 25 | | | | | 30 | | |
| Tyr | Ala | Leu | Val | Pro | Gly | Thr | Ile | Ala | Phe | Thr | Asp | Ala | His | Ile | Glu |
| | | 35 | | | | | 40 | | | | | 45 | | | |
| Val | Asp | Ile | Thr | Tyr | Ala | Glu | Tyr | Phe | Glu | Met | Ser | Val | Arg | Leu | Ala |
| | 50 | | | | | 55 | | | | | 60 | | | | |
| Glu | Ala | Met | Lys | Arg | Tyr | Gly | Leu | Asn | Thr | Asn | His | Arg | Ile | Val | Val |
| 65 | | | | | 70 | | | | | 75 | | | | | 80 |
| Cys | Ser | Glu | Asn | Ser | Leu | Gln | Phe | Phe | Met | Pro | Val | Leu | Gly | Ala | Leu |
| | | | | 85 | | | | | 90 | | | | | 95 | |
| Phe | Ile | Gly | Val | Ala | Val | Ala | Pro | Ala | Asn | Asp | Ile | Tyr | Asn | Glu | Arg |
| | | | 100 | | | | | 105 | | | | | 110 | | |
| Glu | Leu | Leu | Asn | Ser | Met | Gly | Ile | Ser | Gln | Pro | Thr | Val | Val | Phe | Val |
| | | 115 | | | | | 120 | | | | | 125 | | | |
| Ser | Lys | Lys | Gly | Leu | Gln | Lys | Ile | Leu | Asn | Val | Gln | Lys | Lys | Leu | Pro |
| | 130 | | | | | 135 | | | | | 140 | | | | |
| Ile | Ile | Gln | Lys | Ile | Ile | Ile | Met | Asp | Ser | Lys | Thr | Asp | Tyr | Gln | Gly |
| 145 | | | | | 150 | | | | | 155 | | | | | 160 |
| Phe | Gln | Ser | Met | Tyr | Thr | Phe | Val | Thr | Ser | His | Leu | Pro | Pro | Gly | Phe |
| | | | | 165 | | | | | 170 | | | | | 175 | |
| Asn | Glu | Tyr | Asp | Phe | Val | Pro | Glu | Ser | Phe | Asp | Arg | Asp | Lys | Thr | Ile |
| | | | 180 | | | | | 185 | | | | | 190 | | |
| Ala | Leu | Ile | Met | Asn | Ser | Ser | Gly | Ser | Thr | Gly | Leu | Pro | Lys | Gly | Val |
| | | 195 | | | | | 200 | | | | | 205 | | | |
| Ala | Leu | Pro | His | Arg | Thr | Ala | Cys | Val | Arg | Phe | Ser | His | Ala | Arg | Asp |
| | 210 | | | | | 215 | | | | | 220 | | | | |
| Pro | Ile | Phe | Gly | Asn | Gln | Ile | Ile | Pro | Asp | Thr | Ala | Ile | Leu | Ser | Val |
| 225 | | | | | 230 | | | | | 235 | | | | | 240 |
| Val | Pro | Phe | His | His | Gly | Phe | Gly | Met | Phe | Thr | Thr | Leu | Gly | Tyr | Leu |
| | | | | 245 | | | | | 250 | | | | | 255 | |
| Ile | Cys | Gly | Phe | Arg | Val | Val | Leu | Met | Tyr | Arg | Phe | Glu | Glu | Glu | Leu |
| | | | 260 | | | | | 265 | | | | | 270 | | |
| Phe | Leu | Arg | Ser | Leu | Gln | Asp | Tyr | Lys | Ile | Gln | Ser | Ala | Leu | Leu | Val |
| | | 275 | | | | | 280 | | | | | 285 | | | |
| Pro | Thr | Leu | Phe | Ser | Phe | Phe | Ala | Lys | Ser | Thr | Leu | Ile | Asp | Lys | Tyr |
| | 290 | | | | | 295 | | | | | 300 | | | | |
| Asp | Leu | Ser | Asn | Leu | His | Glu | Ile | Ala | Ser | Gly | Gly | Ala | Pro | Leu | Ser |
| 305 | | | | | 310 | | | | | 315 | | | | | 320 |
| Lys | Glu | Val | Gly | Glu | Ala | Val | Ala | Lys | Arg | Phe | His | Leu | Pro | Gly | Ile |
| | | | | 325 | | | | | 330 | | | | | 335 | |
| Arg | Gln | Gly | Tyr | Gly | Leu | Thr | Glu | Thr | Thr | Ser | Ala | Ile | Leu | Ile | Thr |
| | | | 340 | | | | | 345 | | | | | 350 | | |
| Pro | Glu | Gly | Asp | Asp | Lys | Pro | Gly | Ala | Val | Gly | Lys | Val | Val | Pro | Phe |
| | | 355 | | | | | 360 | | | | | 365 | | | |
| Phe | Glu | Ala | Lys | Val | Val | Asp | Leu | Asp | Thr | Gly | Lys | Thr | Leu | Gly | Val |
| | 370 | | | | | 375 | | | | | 380 | | | | |
| Asn | Gln | Arg | Gly | Glu | Leu | Cys | Val | Arg | Gly | Pro | Met | Ile | Met | Ser | Gly |
| 385 | | | | | 390 | | | | | 395 | | | | | 400 |

| | | | | | | | | | | | | | | | | |
|---|---|---|---|---|---|---|---|---|---|---|---|---|---|---|---|---|
|Tyr|Val|Asn|Asn|Pro<br>405|Glu|Ala|Thr|Asn|Ala<br>410|Leu|Ile|Asp|Lys|Asp<br>415|Gly| |
|Trp|Leu|His|Ser<br>420|Gly|Asp|Ile|Ala|Tyr<br>425|Trp|Asp|Glu|Asp<br>430|His|Phe| | |
|Phe|Ile|Val<br>435|Asp|Arg|Leu|Lys|Ser<br>440|Leu|Ile|Lys|Tyr|Lys<br>445|Gly|Tyr|Gln| |
|Val|Ala<br>450|Pro|Ala|Glu|Leu|Glu<br>455|Ser|Ile|Leu|Leu|Gln<br>460|His|Pro|Asn|Ile| |
|Phe<br>465|Asp|Ala|Gly|Val|Ala<br>470|Gly|Leu|Pro|Asp|Asp<br>475|Asp|Ala|Gly|Glu|Leu<br>480| |
|Pro|Ala|Ala|Val|Val<br>485|Val|Leu|Glu|His|Gly<br>490|Lys|Thr|Met|Thr|Glu<br>495|Lys| |
|Glu|Ile|Val|Asp<br>500|Tyr|Val|Ala|Ser|Gln<br>505|Val|Thr|Thr|Ala|Lys<br>510|Lys|Leu| |
|Arg|Gly|Gly<br>515|Val|Val|Phe|Val|Asp<br>520|Glu|Val|Pro|Lys<br>525|Gly|Leu|Thr|Gly| |
|Lys|Leu<br>530|Asp|Ala|Arg|Lys|Ile<br>535|Arg|Glu|Ile|Leu|Ile<br>540|Lys|Ala|Lys|Lys| |
|Gly<br>545|Gly|Lys|Ile|Ala|Val<br>550| | | | | | | | | | | |

( 2 ) INFORMATION FOR SEQ ID NO:5:

( i ) SEQUENCE CHARACTERISTICS:
        ( A ) LENGTH: 1653 base pairs
        ( B ) TYPE: nucleic acid
        ( C ) STRANDEDNESS: single
        ( D ) TOPOLOGY: linear ( i i ) MOLECULE TYPE: cDNA ( v ) FRAGMENT TYPE: C-terminal ( v i ) ORIGINAL SOURCE:
        ( A ) ORGANISM: Photinus pyralis ( i x ) FEATURE:
        ( A ) NAME/KEY: CDS
        ( B ) LOCATION: 1..1650

( x i ) SEQUENCE DESCRIPTION: SEQ ID NO:5:

| | | | | | | | | | | | | | | | | |
|---|---|---|---|---|---|---|---|---|---|---|---|---|---|---|---|---|
|ATG|GTC|ACC|GAC|GCC|AAA|AAC|ATA|AAG|AAA|GGC|CCG|GCG|CCA|TTC|TAT|48|
|Met<br>1|Val|Thr|Asp|Ala<br>5|Lys|Asn|Ile|Lys|Lys<br>10|Gly|Pro|Ala|Pro|Phe<br>15|Tyr| |
|CCG|CTG|GAA|GAT|GGA|ACC|GCT|GGA|GAG|CAA|CTG|CAT|AAG|GCT|ATG|AAG|96|
|Pro|Leu|Glu|Asp<br>20|Gly|Thr|Ala|Gly|Glu<br>25|Gln|Leu|His|Lys|Ala<br>30|Met|Lys| |
|AGA|TAC|GCC|CTG|GTT|CCT|GGA|ACA|ATT|GCT|TTT|ACA|GAT|GCA|CAT|ATC|144|
|Arg|Tyr|Ala<br>35|Leu|Val|Pro|Gly|Thr<br>40|Ile|Ala|Phe|Thr|Asp<br>45|Ala|His|Ile| |
|GAG|GTG|GAC|ATC|ACT|TAC|GCT|GAG|TAC|TTC|GAA|ATG|TCC|GTT|CGG|TTG|192|
|Glu|Val|Asp<br>50|Ile|Thr|Tyr|Ala|Glu<br>55|Tyr|Phe|Glu|Met|Ser<br>60|Val|Arg|Leu| |
|GCA|GAA|GCT|ATG|AAA|CGA|TAT|GGG|CTG|AAT|ACA|AAT|CAC|AGA|ATC|GTC|240|
|Ala|Glu|Ala|Met|Lys<br>65|Arg|Tyr|Gly|Leu|Asn<br>70|Thr|Asn|His|Arg|Ile<br>75|Val<br>80| |
|GTA|TGC|AGT|GAA|AAC|TCT|CTT|CAA|TTC|TTT|ATG|CCG|GTG|TTG|GGC|GCG|288|
|Val|Cys|Ser|Glu|Asn<br>85|Ser|Leu|Gln|Phe|Phe<br>90|Met|Pro|Val|Leu|Gly<br>95|Ala| |
|TTA|TTT|ATC|GGA|GTT|GCA|GTT|GCG|CCC|GCG|AAC|GAC|ATT|TAT|AAT|GAA|336|
|Leu|Phe|Ile|Gly<br>100|Val|Ala|Val|Ala|Pro<br>105|Ala|Asn|Asp|Ile|Tyr<br>110|Asn|Glu| |

```
CGT GAA TTG CTC AAC AGT ATG GGC ATT TCG CAG CCT ACC GTG GTG TTC    384
Arg Glu Leu Leu Asn Ser Met Gly Ile Ser Gln Pro Thr Val Val Phe
        115                 120                 125

GTT TCC AAA AAG GGG TTG CAA AAA ATT TTG AAC GTG CAA AAA AAG CTC    432
Val Ser Lys Lys Gly Leu Gln Lys Ile Leu Asn Val Gln Lys Lys Leu
        130                 135                 140

CCA ATC ATC CAA AAA ATT ATT ATC ATG GAT TCT AAA ACG GAT TAC CAG    480
Pro Ile Ile Gln Lys Ile Ile Ile Met Asp Ser Lys Thr Asp Tyr Gln
145             150                 155                 160

GGA TTT CAG TCG ATG TAC ACG TTC GTC ACA TCT CAT CTA CCT CCC GGT    528
Gly Phe Gln Ser Met Tyr Thr Phe Val Thr Ser His Leu Pro Pro Gly
                165                 170                 175

TTT AAT GAA TAC GAT TTT GTG CCA GAG TCC TTC GAT AGG GAC AAG ACA    576
Phe Asn Glu Tyr Asp Phe Val Pro Glu Ser Phe Asp Arg Asp Lys Thr
            180                 185                 190

ATT GCA CTG ATC ATG AAC TCC TCT GGA TCT ACT GGT CTG CCT AAA GGT    624
Ile Ala Leu Ile Met Asn Ser Ser Gly Ser Thr Gly Leu Pro Lys Gly
        195                 200                 205

GTC GCT CTG CCT CAT AGA ACT GCC TGC GTG AGA TTC TCG CAT GCC AGA    672
Val Ala Leu Pro His Arg Thr Ala Cys Val Arg Phe Ser His Ala Arg
210                 215                 220

GAT CCT ATT TTT GGC AAT CAA ATC ATT CCG GAT ACT GCG ATT TTA AGT    720
Asp Pro Ile Phe Gly Asn Gln Ile Ile Pro Asp Thr Ala Ile Leu Ser
225             230                 235                 240

GTT GTT CCA TTC CAT CAC GGT TTT GGA ATG TTT ACT ACA CTC GGA TAT    768
Val Val Pro Phe His His Gly Phe Gly Met Phe Thr Thr Leu Gly Tyr
                245                 250                 255

TTG ATA TGT GGA TTT CGA GTC GTC TTA ATG TAT AGA TTT GAA GAA GAG    816
Leu Ile Cys Gly Phe Arg Val Val Leu Met Tyr Arg Phe Glu Glu Glu
            260                 265                 270

CTG TTT CTG AGG AGC CTT CAG GAT TAC AAG ATT CAA AGT GCG CTG CTG    864
Leu Phe Leu Arg Ser Leu Gln Asp Tyr Lys Ile Gln Ser Ala Leu Leu
        275                 280                 285

GTG CCA ACC CTA TTC TCC TTC TTC GCC AAA AGC ACT CTG ATT GAC AAA    912
Val Pro Thr Leu Phe Ser Phe Phe Ala Lys Ser Thr Leu Ile Asp Lys
290                 295                 300

TAC GAT TTA TCT AAT TTA CAC GAA ATT GCT TCT GGT GGC GCT CCC CTC    960
Tyr Asp Leu Ser Asn Leu His Glu Ile Ala Ser Gly Gly Ala Pro Leu
305             310                 315                 320

TCT AAG GAA GTC GGG GAA GCG GTT GCC AAG AGG TTC CAT CTG CCA GGT    1008
Ser Lys Glu Val Gly Glu Ala Val Ala Lys Arg Phe His Leu Pro Gly
                325                 330                 335

ATC AGG CAA GGA TAT GGG CTC ACT GAG ACT ACA TCA GCT ATT CTG ATT    1056
Ile Arg Gln Gly Tyr Gly Leu Thr Glu Thr Thr Ser Ala Ile Leu Ile
            340                 345                 350

ACA CCC GAG GGG GAT GAT AAA CCG GGC GCG GTC GGT AAA GTT GTT CCA    1104
Thr Pro Glu Gly Asp Asp Lys Pro Gly Ala Val Gly Lys Val Val Pro
        355                 360                 365

TTT TTT GAA GCG AAG GTT GTG GAT CTG GAT ACC GGG AAA ACG CTG GGC    1152
Phe Phe Glu Ala Lys Val Val Asp Leu Asp Thr Gly Lys Thr Leu Gly
370                 375                 380

GTT AAT CAA AGA GGC GAA CTG TGT GTG AGA GGT CCT ATG ATT ATG TCC    1200
Val Asn Gln Arg Gly Glu Leu Cys Val Arg Gly Pro Met Ile Met Ser
385             390                 395                 400

GGT TAT GTA AAC AAT CCG GAA GCG ACC AAC GCC TTG ATT GAC AAG GAT    1248
Gly Tyr Val Asn Asn Pro Glu Ala Thr Asn Ala Leu Ile Asp Lys Asp
                405                 410                 415

GGA TGG CTA CAT TCT GGA GAC ATA GCT TAC TGG GAC GAA GAC GAA CAC    1296
Gly Trp Leu His Ser Gly Asp Ile Ala Tyr Trp Asp Glu Asp Glu His
            420                 425                 430
```

```
TTC  TTC  ATC  GTT  GAC  CGC  CTG  AAG  TCT  CTG  ATT  AAG  TAC  AAA  GGC  TAT              1344
Phe  Phe  Ile  Val  Asp  Arg  Leu  Lys  Ser  Leu  Ile  Lys  Tyr  Lys  Gly  Tyr
          435                      440                     445

CAG  GTG  GCT  CCC  GCT  GAA  TTG  GAA  TCC  ATC  TTG  CTC  CAA  CAC  CCC  AAC              1392
Gln  Val  Ala  Pro  Ala  Glu  Leu  Glu  Ser  Ile  Leu  Leu  Gln  His  Pro  Asn
     450                      455                     460

ATC  TTC  GAC  GCA  GGT  GTC  GCA  GGT  CTT  CCC  GAC  GAT  GAC  GCC  GGT  GAA              1440
Ile  Phe  Asp  Ala  Gly  Val  Ala  Gly  Leu  Pro  Asp  Asp  Asp  Ala  Gly  Glu
465                      470                     475                          480

CTT  CCC  GCC  GCC  GTT  GTT  GTT  TTG  GAG  CAC  GGA  AAG  ACG  ATG  ACG  GAA              1488
Leu  Pro  Ala  Ala  Val  Val  Val  Leu  Glu  His  Gly  Lys  Thr  Met  Thr  Glu
                    485                      490                     495

AAA  GAG  ATC  GTG  GAT  TAC  GTC  GCC  AGT  CAA  GTA  ACA  ACC  GCG  AAA  AAG              1536
Lys  Glu  Ile  Val  Asp  Tyr  Val  Ala  Ser  Gln  Val  Thr  Thr  Ala  Lys  Lys
               500                      505                     510

TTG  CGC  GGA  GGA  GTT  GTG  TTT  GTG  GAC  GAA  GTA  CCG  AAA  GGT  CTT  ACC              1584
Leu  Arg  Gly  Gly  Val  Val  Phe  Val  Asp  Glu  Val  Pro  Lys  Gly  Leu  Thr
          515                      520                     525

GGA  AAA  CTC  GAC  GCA  AGA  AAA  ATC  AGA  GAG  ATC  CTC  ATA  AAG  GCC  AAG              1632
Gly  Lys  Leu  Asp  Ala  Arg  Lys  Ile  Arg  Glu  Ile  Leu  Ile  Lys  Ala  Lys
     530                      535                     540

AAG  GGC  GGA  AAG  ATC  GCC  GTG                                                           1653
Lys  Gly  Gly  Lys  Ile  Ala  Val
545                      550
```

( 2 ) INFORMATION FOR SEQ ID NO:6:

( i ) SEQUENCE CHARACTERISTICS:
        ( A ) LENGTH: 550 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Val  Thr  Asp  Ala  Lys  Asn  Ile  Lys  Lys  Gly  Pro  Ala  Pro  Phe  Tyr
1                        5                    10                          15

Pro  Leu  Glu  Asp  Gly  Thr  Ala  Gly  Glu  Gln  Leu  His  Lys  Ala  Met  Lys
               20                      25                      30

Arg  Tyr  Ala  Leu  Val  Pro  Gly  Thr  Ile  Ala  Phe  Thr  Asp  Ala  His  Ile
          35                      40                      45

Glu  Val  Asp  Ile  Thr  Tyr  Ala  Glu  Tyr  Phe  Glu  Met  Ser  Val  Arg  Leu
     50                      55                      60

Ala  Glu  Ala  Met  Lys  Arg  Tyr  Gly  Leu  Asn  Thr  Asn  His  Arg  Ile  Val
65                       70                      75                          80

Val  Cys  Ser  Glu  Asn  Ser  Leu  Gln  Phe  Phe  Met  Pro  Val  Leu  Gly  Ala
                    85                      90                      95

Leu  Phe  Ile  Gly  Val  Ala  Val  Ala  Pro  Ala  Asn  Asp  Ile  Tyr  Asn  Glu
               100                     105                     110

Arg  Glu  Leu  Leu  Asn  Ser  Met  Gly  Ile  Ser  Gln  Pro  Thr  Val  Val  Phe
          115                     120                     125

Val  Ser  Lys  Lys  Gly  Leu  Gln  Lys  Ile  Leu  Asn  Val  Gln  Lys  Lys  Leu
     130                     135                     140

Pro  Ile  Ile  Gln  Lys  Ile  Ile  Met  Asp  Ser  Lys  Thr  Asp  Tyr  Gln
145                      150                     155                     160

Gly  Phe  Gln  Ser  Met  Tyr  Thr  Phe  Val  Thr  Ser  His  Leu  Pro  Pro  Gly
                    165                     170                     175

Phe  Asn  Glu  Tyr  Asp  Phe  Val  Pro  Glu  Ser  Phe  Asp  Arg  Asp  Lys  Thr
               180                     185                     190
```

Ile Ala Leu Ile Met Asn Ser Ser Gly Ser Thr Gly Leu Pro Lys Gly
        195                 200                 205

Val Ala Leu Pro His Arg Thr Ala Cys Val Arg Phe Ser His Ala Arg
    210                 215                 220

Asp Pro Ile Phe Gly Asn Gln Ile Ile Pro Asp Thr Ala Ile Leu Ser
225                 230                 235                 240

Val Val Pro Phe His His Gly Phe Gly Met Phe Thr Thr Leu Gly Tyr
                245                 250                 255

Leu Ile Cys Gly Phe Arg Val Val Leu Met Tyr Arg Phe Glu Glu Glu
            260                 265                 270

Leu Phe Leu Arg Ser Leu Gln Asp Tyr Lys Ile Gln Ser Ala Leu Leu
        275                 280                 285

Val Pro Thr Leu Phe Ser Phe Ala Lys Ser Thr Leu Ile Asp Lys
    290                 295                 300

Tyr Asp Leu Ser Asn Leu His Glu Ile Ala Ser Gly Gly Ala Pro Leu
305                 310                 315                 320

Ser Lys Glu Val Gly Glu Ala Val Ala Lys Arg Phe His Leu Pro Gly
                325                 330                 335

Ile Arg Gln Gly Tyr Gly Leu Thr Glu Thr Thr Ser Ala Ile Leu Ile
            340                 345                 350

Thr Pro Glu Gly Asp Asp Lys Pro Gly Ala Val Gly Lys Val Val Pro
        355                 360                 365

Phe Phe Glu Ala Lys Val Val Asp Leu Asp Thr Gly Lys Thr Leu Gly
    370                 375                 380

Val Asn Gln Arg Gly Glu Leu Cys Val Arg Gly Pro Met Ile Met Ser
385                 390                 395                 400

Gly Tyr Val Asn Asn Pro Glu Ala Thr Asn Ala Leu Ile Asp Lys Asp
                405                 410                 415

Gly Trp Leu His Ser Gly Asp Ile Ala Tyr Trp Asp Glu Asp Glu His
            420                 425                 430

Phe Phe Ile Val Asp Arg Leu Lys Ser Leu Ile Lys Tyr Lys Gly Tyr
        435                 440                 445

Gln Val Ala Pro Ala Glu Leu Glu Ser Ile Leu Leu Gln His Pro Asn
450                 455                 460

Ile Phe Asp Ala Gly Val Ala Gly Leu Pro Asp Asp Ala Gly Glu
465                 470                 475                 480

Leu Pro Ala Ala Val Val Val Leu Glu His Gly Lys Thr Met Thr Glu
                485                 490                 495

Lys Glu Ile Val Asp Tyr Val Ala Ser Gln Val Thr Thr Ala Lys Lys
            500                 505                 510

Leu Arg Gly Gly Val Val Phe Val Asp Glu Val Pro Lys Gly Leu Thr
        515                 520                 525

Gly Lys Leu Asp Ala Arg Lys Ile Arg Glu Ile Leu Ile Lys Ala Lys
    530                 535                 540

Lys Gly Gly Lys Ile Ala
545                 550

(2) INFORMATION FOR SEQ ID NO:7:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (v) FRAGMENT TYPE: C-terminal (vi) ORIGINAL SOURCE:
    (A) ORGANISM: Photinus pyralis (ix) FEATURE:
    (A) NAME/KEY: CDS
    (B) LOCATION: 1..22

(xi) SEQUENCE DESCRIPTION: SEQ ID NO:7:

```
TTC  TAT  CCG  CTG  GAA  GAT  GGA  A                                22
Phe  Tyr  Pro  Leu  Glu  Asp  Gly
 1               5
```

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:8:

```
Phe  Tyr  Pro  Leu  Glu  Asp  Gly
 1               5
```

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (v) FRAGMENT TYPE: C-terminal (vi) ORIGINAL SOURCE:
        (A) ORGANISM: Photinus pyralis (ix) FEATURE:
        (A) NAME/KEY: CDS
        (B) LOCATION: 1..12

(xi) SEQUENCE DESCRIPTION: SEQ ID NO:9:

```
GTG  GTG  TTC  GTT                                                  12
Val  Val  Phe  Val
 1
```

(2) INFORMATION FOR SEQ ID NO:10:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:10:

```
Val  Val  Phe  Val
 1
```

(2) INFORMATION FOR SEQ ID NO:11:

(i) SEQUENCE CHARACTERISTICS:
        (A) LENGTH: 8 base pairs
        (B) TYPE: nucleic acid
        (C) STRANDEDNESS: single
        (D) TOPOLOGY: linear ( i i ) MOLECULE TYPE: cDNA ( v ) FRAGMENT TYPE: C-terminal ( v i ) ORIGINAL SOURCE:
    ( A ) ORGANISM: Photinus pyralis ( i x ) FEATURE:
    ( A ) NAME/KEY: CDS
    ( B ) LOCATION: 1..8

( x i ) SEQUENCE DESCRIPTION: SEQ ID NO:11:

```
TGC CGT AG                                                                 8
Cys Arg
  1
```

( 2 ) INFORMATION FOR SEQ ID NO:12:

( i ) SEQUENCE CHARACTERISTICS:
    ( A ) LENGTH: 2 amino acids
    ( B ) TYPE: amino acid
    ( D ) TOPOLOGY: linear ( i i ) MOLECULE TYPE: protein ( x i ) SEQUENCE DESCRIPTION: SEQ ID NO:12:

```
Cys Arg
  1
```

( 2 ) INFORMATION FOR SEQ ID NO:13:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( v ) FRAGMENT TYPE: C-terminal ( v i ) ORIGINAL SOURCE:
    ( A ) ORGANISM: Photinus pyralis ( i x ) FEATURE:
    ( A ) NAME/KEY: CDS
    ( B ) LOCATION: 1..25

( x i ) SEQUENCE DESCRIPTION: SEQ ID NO:13:

```
AAG AGG CGA ACT GTG TGT GAG AGG T                                         25
Lys Arg Arg Thr Val Cys Glu Arg
  1               5
```

( 2 ) INFORMATION FOR SEQ ID NO:14:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: protein ( x i ) SEQUENCE DESCRIPTION: SEQ ID NO:14:

```
Lys Arg Arg Thr Val Cys Glu Arg
  1               5
```

( 2 ) INFORMATION FOR SEQ ID NO:15:

( i ) SEQUENCE CHARACTERISTICS:
    ( A ) LENGTH: 10 base pairs
    ( B ) TYPE: nucleic acid ( C ) STRANDEDNESS: single
              ( D ) TOPOLOGY: linear ( i i ) MOLECULE TYPE: cDNA ( v ) FRAGMENT TYPE: C-terminal ( v i ) ORIGINAL SOURCE:
              ( A ) ORGANISM: Photinus pyralis ( i x ) FEATURE:
              ( A ) NAME/KEY: CDS
              ( B ) LOCATION: 1..10

( x i ) SEQUENCE DESCRIPTION: SEQ ID NO:15:

```
CAG  GTG  TCG  C                                                        10
Gln  Val  Ser
 1
```

( 2 ) INFORMATION FOR SEQ ID NO:16:

( i ) SEQUENCE CHARACTERISTICS:
              ( A ) LENGTH: 3 amino acids
              ( B ) TYPE: amino acid
              ( D ) TOPOLOGY: linear ( i i ) MOLECULE TYPE: protein ( x i ) SEQUENCE DESCRIPTION: SEQ ID NO:16:

```
Gln  Val  Ser
 1
```

( 2 ) INFORMATION FOR SEQ ID NO:17:

( i ) SEQUENCE CHARACTERISTICS:
              ( A ) LENGTH: 9 base pairs
              ( B ) TYPE: nucleic acid
              ( C ) STRANDEDNESS: single
              ( D ) TOPOLOGY: linear ( i i ) MOLECULE TYPE: cDNA ( v ) FRAGMENT TYPE: C-terminal ( v i ) ORIGINAL SOURCE:
              ( A ) ORGANISM: Photinus pyralis ( i x ) FEATURE:
              ( A ) NAME/KEY: CDS
              ( B ) LOCATION: 1..9

( x i ) SEQUENCE DESCRIPTION: SEQ ID NO:17:

```
GAC  ATC  ACT                                                            9
Asp  Ile  Thr
 1
```

( 2 ) INFORMATION FOR SEQ ID NO:18:

( i ) SEQUENCE CHARACTERISTICS:
              ( A ) LENGTH: 3 amino acids
              ( B ) TYPE: amino acid
              ( D ) TOPOLOGY: linear ( i i ) MOLECULE TYPE: protein ( x i ) SEQUENCE DESCRIPTION: SEQ ID NO:18:

```
Asp  Ile  Thr
 1
```

( 2 ) INFORMATION FOR SEQ ID NO:19:

( i ) SEQUENCE CHARACTERISTICS:

```
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: cDNA ( v ) FRAGMENT TYPE: C-terminal ( v i ) ORIGINAL SOURCE:
        ( A ) ORGANISM: Photinus pyralis ( i x ) FEATURE:
        ( A ) NAME/KEY: CDS
        ( B ) LOCATION: 1..9

( x i ) SEQUENCE DESCRIPTION: SEQ ID NO:19:

GGC  ATT  TCG                                                                    9
Gly  Ile  Ser
 1

( 2 ) INFORMATION FOR SEQ ID NO:20:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

Gly  Ile  Ser
 1
```

MODIFIED LUCIFERASE

FIELD OF THE INVENTION

The present invention relates to genetic reporters. Specifically, the present invention is directed to a reporter system utilizing a modified form of beetle luciferase and the gene encoding the modified luciferase. The present invention is also directed to a method of producing the gene encoding the novel modified luciferase.

CITED REFERENCES

A full bibliographic citation of the references cited in this application can be found in the section preceding the nucleotide Sequence Listings.

DESCRIPTION OF THE PRIOR ART

Bioluminescence is the light produced in certain organisms as a result of luciferase-mediated oxidation reactions. The luciferase genes, e.g., the genes from luminous beetle and, in particular, the luciferase from *Photinus pyralis* (the common firefly of North America), are currently the most popular luminescent reporter genes. Reference is made to Bronstein, et al. (1994) for a review of luminescent reporter gene assays.

Firefly luciferase has become highly valuable as a genetic reporter due to the convenience, sensitivity and linear range of the luminescence assay. Today, luciferase is used in virtually every experimental biological system, including prokaryotic and eukaryotic cell culture, transgenic plants and animals, and cell-free expression systems.

Although referred to simply as firefly luciferase, the enzyme is derived from a specific North American beetle, *Photinus pyralis*. The enzyme is a monomeric protein (62 kDa) which generates light through monooxygenation of beetle luciferin utilizing ATP and $O_2$.

The gene encoding luciferase was cloned from *Photinus pyralis*, and demonstrated to produce active enzyme in *E. coli* (de Wet, et al., 1987). The cDNA encoding luciferase (luc) continues to gain favor as the gene of choice for reporting genetic activity in animal, plant and microbial cells. The luciferase reaction, modified by the addition of CoA to produce persistent light emission, provides an extremely sensitive and rapid in vitro assay for quantifying luciferase expression in small samples of transfected cells or tissues.

Normally, in the firefly light organ, luciferase is located in specialized peroxisomes of the photocytic cells. When expressed in foreign hosts, a conserved translocation signal within the enzyme structure cause it to accumulate in peroxisomes and glycosomes. In moderate to high levels of expression, the peroxisomes typically become saturated with luciferase, and much of the reporter is found in the cytoplasm (Keller, G. A. et al, 1987). This creates the undesirable circumstance of having the reporter present in two different subcellular compartments, each having potentially different physiological characteristics.

To use luciferase as a genetic reporter, extracts of cells expressing luciferase are mixed with substrates (beetle luciferin, $Mg^{2+}$ATP, and $O_2$), and luminescence is measured immediately. The assay is very rapid and sensitive, providing gene expression data with little effort. The conventional luciferase assay has been further improved by including coenzyme A in the assay reagent to yield greater enzyme turnover and thus greater luminescence intensity (Promega Luciferase Assay Reagent, Cat.# E1500, Promega Corporation, Madison, Wis.). Using this reagent, luciferase activity can be readily measured in luminometers or scintillation counters without the need of a reagent injection device. Luciferase activity can also be detected in living cells by adding luciferin to the growth medium. This in vivo luminescence relies on the ability of beetle luciferin to diffuse through cellular and peroxisomal membranes and on the intracellular availability of ATP and $O_2$ in the cytosol and peroxisome.

Despite its utility as a reporter, however, luciferase has naturally evolved for the nocturnal mating behavior of beetles and not for the convenience of experimental molecular biologists. Thus, it is not necessarily optimized for the wide variety of host organisms in which it is presently being used.

Further, the growing interest in using luciferase as a real-time, i.e., in vivo, reporter of gene expression in eukaryotic cells has raised concerns that i) the activity of luciferase, which is sequestered in peroxisomes, may suffer from limited substrate availability, and ii) high-level accumulation of luciferase in peroxisomes may adversely affect the physiological well-being of the host cell.

The major limitation may be that luciferase is a peroxisomal enzyme which may impact cellular physiology in some hosts. Localization to the peroxisomes can interfere with normal cellular physiology in two ways. First, large amounts of a foreign protein in the peroxisomes could impair their normal function. Second, many other peroxisomal proteins utilize the same translocation signals (Gould, S. J. et al. 1989), and thus, saturation with luciferase import implies competition for the import of other peroxisomal proteins.

Peroxisomal location of luciferase may also interfere with the performance of the genetic reporter. For instance, the luciferase accumulation in the cell could be differentially affected if it is distributed into two different subcellular compartments. The stability of luciferase in peroxisomes is not known, but may well be different than its stability in the cytosol. If so, the apparent expression of luciferase could be affected by changes in the distribution of luciferase between peroxisomes and the cytosol. Measurements of in vivo luminescence could also be affected since the availability of ATP, $O_2$, and luciferin within peroxisomes is not known. In particular, the concentration of luciferin could be limited by the need to diffuse across both the cytoplasmic and peroxisomal membranes. This partitioning of luciferase between different intracellular compartments may add unforeseen variability when comparing luciferase activities derived from genetic expression elements with different transcriptional activities.

SUMMARY OF THE INVENTION

To create a genetic reporter more generally suitable and convenient for diverse applications, the present invention is directed to mutated forms of the luciferase cDNA (luc; referred to as the "luciferase gene"). The mutated forms of luc, designated luc+ and luc+NF, contain multiple new features. Chief among these is removal of the peroxisomal translocation sequence to yield a cytoplasmic form of the enzyme. Other changes include removal of potentially genetic regulatory sites and inconvenient endonuclease restriction sites from within the gene, and improvement of the codon usage for mammalian and plant cells. The modified luciferase reporter enzyme is also devoid of two potential N-glycosylation targets, thus minimizing unpredictable structural modifications due to post-translational glycosylation. A related gene, luc+NF, has also been developed to allow optimal production of N-terminal fusion proteins.

The present invention is specifically directed to a luciferase gene encoding a modified form of the luciferase of the *Photinus pyralis*, wherein at least one of the following changes appear:

a. an internal palindrome is eliminated by changing the DNA sequence beginning at nucleotide 40 from TTC TAT CCT CTA GAG GAT GGA A to TTC TAT CCG CTG GAA GAT GGA A.

b. an internal palindrome is eliminated by changing the DNA sequence beginning at nucleotide 945 from GGG CGC ACC TCT TTC GAA A to TGG CGC TCC CCT CTC TAA G;

c. a palindrome is eliminated by changing the DNA sequence beginning at nucleotide 1302 from AGT TGA CCG CTT GAA GTC TTT AAT TAA ATA C to CGT TGA CCG GAA GTC TCT GAT TAA GTA C;

d. the Xba I restriction site is removed by changing the DNA sequence at nucleotide 48 from TC TAG A to GC TGG A, wherein such change is conducted without affecting the amino acid sequence;

e. the EcoR I restriction site is removed by changing the DNA sequence at nucleotide 583 from ATA ATG AAT TTC to ATC ATG AAC TCC, wherein such change is conducted without affecting the amino acid sequence;

f. the potential TGT-3 site is removed by changing the DNA sequence at nucleotide 373 from GTA GTG TTT GTT to GTG GTG TTC GTT, wherein such change is conducted without affecting the amino acid sequence;

g. the BstE II restriction site is removed by changing the DNA sequence at nucleotide 608 from GGT TAC CTA to GTC TGC CTA, wherein such change is conducted without affecting the amino acid sequence;

h. the EcoR V restriction site is removed by changing the DNA sequence at nucleotide 1333 from AAA GGA TAT CAG GTG GCC to AAA GGC TAT CAG GTG GCT, wherein such change is conducted without affecting the amino acid sequence;

i. the Cla I restriction site is removed by changing the DNA sequence at nucleotide 1365 from ATC GAT ATT GTT A to ATC CAT CTT GCT C, wherein such change is conducted without affecting the amino acid sequence;

j. the potential AP1 restriction site is removed by changing the DNA sequence at nucleotide 646 from TGC GTC AG to TGC CGT AG, wherein such change is conducted without affecting the amino acid sequence;

k. the potential AP1 restriction site is removed by changing the DNA sequence at nucleotide 1158 from GAG AGG CGA ATT ATG TGT CAG AGG A to AAG AGG CGA ACT GTG TGT GAG AGG T, wherein such change is conducted without affecting the amino acid sequence;

l. the potential AP1 and Sp1 restriction sites are removed by changing the DNA sequence at nucleotide 1400 from CGG GCG TGG C to CAG GTG TCG C, wherein such change is conducted without affecting the amino acid sequence;

m. the glycosylation site beginning at amino acid 50 is eliminated by replacing asparagine with aspartate;

n. the glycosylation site beginning at amino acid 50 is eliminated by replacing the tripeptide codon sequence AAC ATC ACG with GAC ATC ACT, such that the amino acid sequence asparagine-isoleucine-threonine is replaced with aspartate-isoleucine-threonine;

o. the glycosylation site beginning at amino acid 119 is eliminated by replacing asparagine with glycine; and p. the glycosylation site beginning at amino acid 119 is eliminated by replacing the tripeptide codon sequence AAC ATT TCG with GGC ATT TCG, such that the amino acid sequence asparagine-isoleucine-serine is replaced with glycine-isoleucine-serine.

Additionally, the present invention is directed to a recombinant DNA sequence containing the luciferase gene described above, and to a host cell containing the recombinant DNA.

The present invention is also directed to a luciferase gene encoding a modified form of the luciferase of *Photinus pyralis*, wherein at least one of the following changes appear:

a. the pentapeptide sequence glycine-lysine-serine-lysine-leucine at the C-terminal end is replaced by the tripeptide glycine-lysine-threonine; or b. the tripeptide sequence serine-lysine-leucine at the C-terminal end is replaced by isoleucine-alanine-valine.

The present invention is also directed to a modified luciferase gene having the following nucleotide sequence and amino acid sequence as illustrated in Sequence Listings SEQ ID: No. 3 and SEQ. ID: No. 4, respectively, and a protein sequence encoded by the modified luciferase gene.

The present invention is further directed to a modified luciferase gene having the following nucleotide sequence as illustrated in Sequence Listing SEQ ID: No. 3 and a protein sequence encoded by modified luciferase gene.

The present invention is also directed to a process for increasing the expression of a luciferase gene, comprising removing the peroxisomal translocation sequence in the nucleotide sequence to yield a cytoplasmic form of the enzyme.

The present invention is also directed to a process for eliminating the influence of peroxisomes on the expression of a luciferase gene, comprising removing the peroxisomal translocation sequence by mutating the nucleotide sequence to yield a cytoplasmic form of the enzyme.

The primary advantage conferred by this invention is the availability of a modified luciferase reporter gene that is superior in performance and usefulness to currently used cDNA sequences coding beetle luciferase. The present invention will set a new standard for eukaryotic and prokaryotic reporter technology.

A summary of the major benefits of this invention are as follows:

1. in vivo expression unbiased by peroxisomal physiology in eukaryotic cells;

2. in vivo expression levels higher than currently achievable with native firefly luciferase reporter genes in many eukaryotic cell types;

3. a reporter gene that is genetically neutral, containing no major genetic regulatory elements or palindromic RNA sequences; and 4. greater reliability and convenience as a genetic reporter in diverse research applications.

DETAILED DESCRIPTION OF THE INVENTION

Definitions

Figure 1:
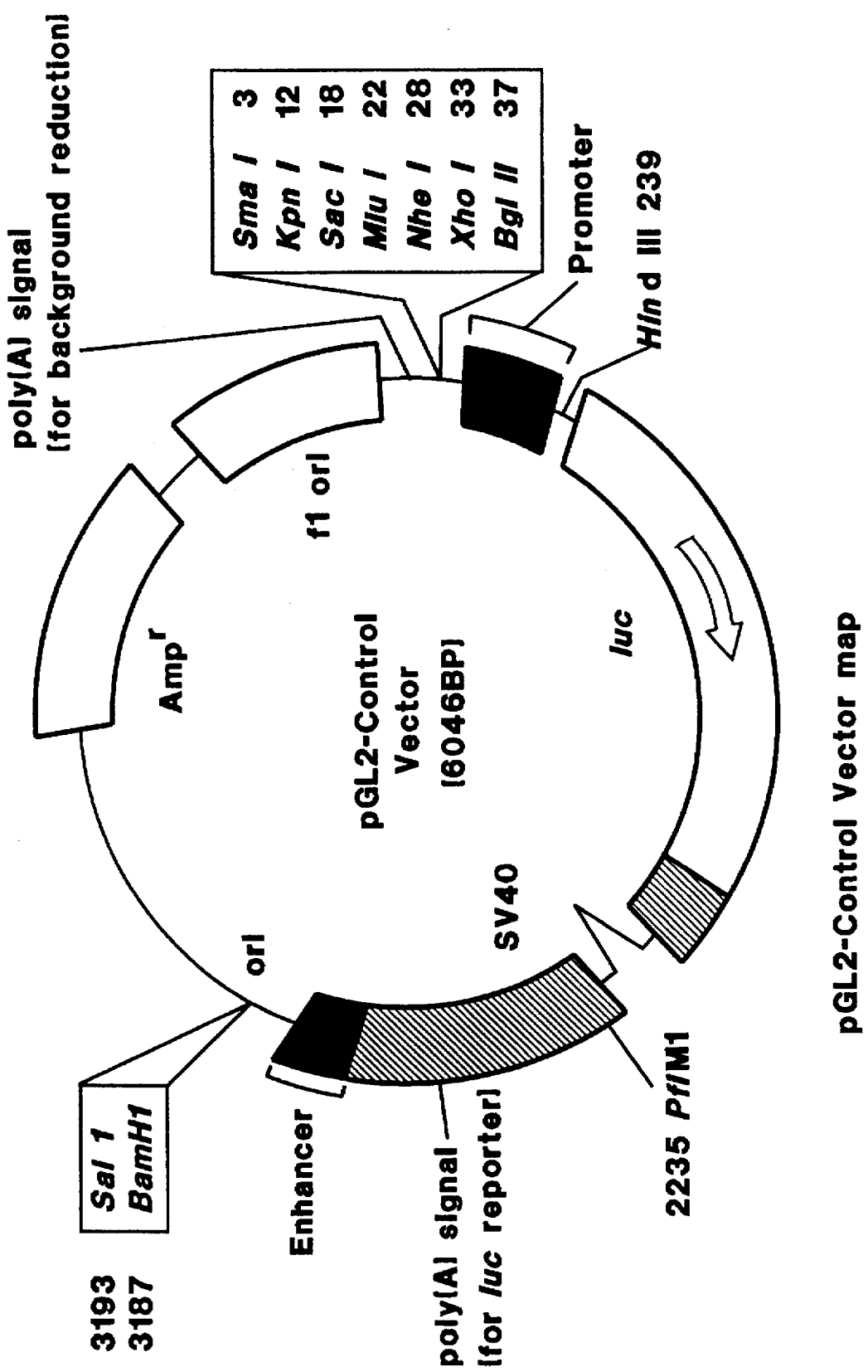
FIG. 1 shows a genetic map of a recombinant plasmid pGL2-Control.

The following definition is provided to assist in providing a clear and consistent understanding of the scope and detail of the terms:

Amino Acids:

Amino acids are shown either by three letter or one letter abbreviations as follows:

| Abbreviated Designation | Amino Acid |
| --- | --- |
| A Ala | Alanine |
| C Cys | Cysteine |
| D Asp | Aspartic acid |
| E Glu | Glutamic acid |
| F Phe | Phenylalanine |
| G Gly | Glycine |
| H His | Histidine |
| I Ile | Isoleucine |
| K Lys | Lysine |
| L Leu | Leucine |
| M Met | Methionine |
| N Asn | Asparagine |
| P Pro | Proline |
| Q Gln | Glutamine |
| R Arg | Arginine |
| S Ser | Serine |
| T Thr | Threonine |
| V Val | Valine |
| W Trp | Tryptophan |
| Y Tyr | Tyrosine |

Beetle Luciferase

The present invention is directed to a luciferase gene which encodes a modified form of beetle luciferase. For purposes of this invention, beetle luciferase includes, but is not limited to, any luciferase from a luminous beetle, including beetles of the families: Elateridae (click beetles), Phengodidae (glow worms), and Lampyridae (fireflies). All of these beetles produce light by oxidation of beetle luciferin, and all contain a translocation signal for peroxisomes. Unless otherwise directed in this disclosure, there is no wish to limit the term luciferase to one species or variety of beetle. For purposes of explanation and example, reference will be primarily directed to luciferase from the North American firefly (*Photinus pyralis*).

Unmodified Luciferase Enzyme

To improve the general suitability of luciferase as a genetic reporter, a modified form of the luciferase gene from the common North American firefly *Photinus pyralis* has been developed. The luciferase gene derived from *Photinus pyralis* has been extensively studied (see de Wet, et al., 1987). Firefly luciferase has an apparent molecular weight of 62 kilodaltons (kD) and requires luciferin, ATP, and $O_2$ as substrates.

The nucleotide sequence of luc, and amino acid sequence of the encoded luciferase, are shown in Sequence Listings SEQ ID: No. 1 and SEQ ID: No. 2, which are also found in de Wet, et al. (1987). Amino acids in the native luciferase are numbered starting with "1" at the initiating methionine (de Wet, et al., 1987). Nucleotides in the luciferase gene are numbered starting with "1" at the "A" of ATG(Met).

Modifications to luc

The purpose of the modifications to luc was to minimize potential biological interferences that may complicate the interpretation of reporter data. The strategy was to develop an optimal cytoplasmic form of the luciferase gene by making one or more alterations to the luc gene structure as follows:

Removal of tripeptide sequence "serine-lysine-leucine: The present invention is directed to the ability to increase reporter signal strength and eliminate the influence of peroxisomal physiology by removing the C-terminal amino acids. The amino acid sequence of the native luciferase protein contains the C-terminal tripeptide "serine-lysine-leucine" (-Ser-Lys-Leu), which is well established to be a peroxisome targeting sequence (Keller, et al., 1987, infra.). Removal of this sequence abolishes import into peroxisomes and therefore peroxisomal targeting (Gould, S. J. et al., 1989). However, the effect of removing this sequence on luciferase expression or the specific activity of this modified luciferase has not been determined. This modification alters the structure of both the gene and enzyme.

All mutations to the luciferase cDNA of *Photinus pyralis* were performed using oligonucleotide-mediated, site specific mutagenesis directed against single-stranded plasmid templates according to the method of Lewis and Thompson (1990). According to this method, a mutagenic primer designed to correct a defective ampicillin resistance gene is used in combination with one or more primers designed to mutate discreet regions within the target gene. Rescued antibiotic resistance coupled with distant non-selectable mutations in the target gene results in high frequency capture of the desired mutations.

Figure 2:
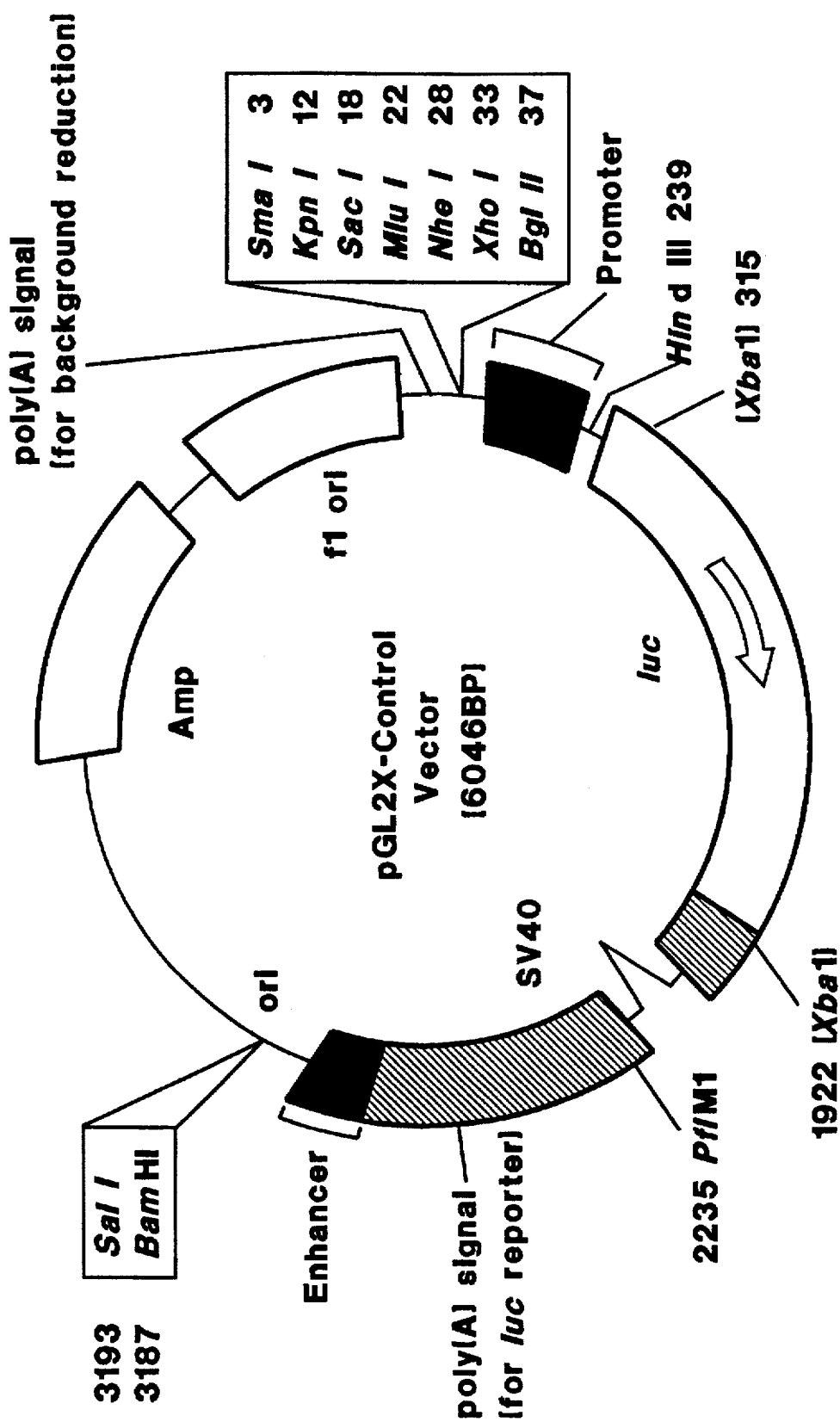
FIG. 2 shows a genetic map of a recombinant plasmid pGL2X constructed by introducing an Xba I restriction site at the immediate 3' end of the luc cDNA contained in the pGL2-Control Vector.
Figure 3:
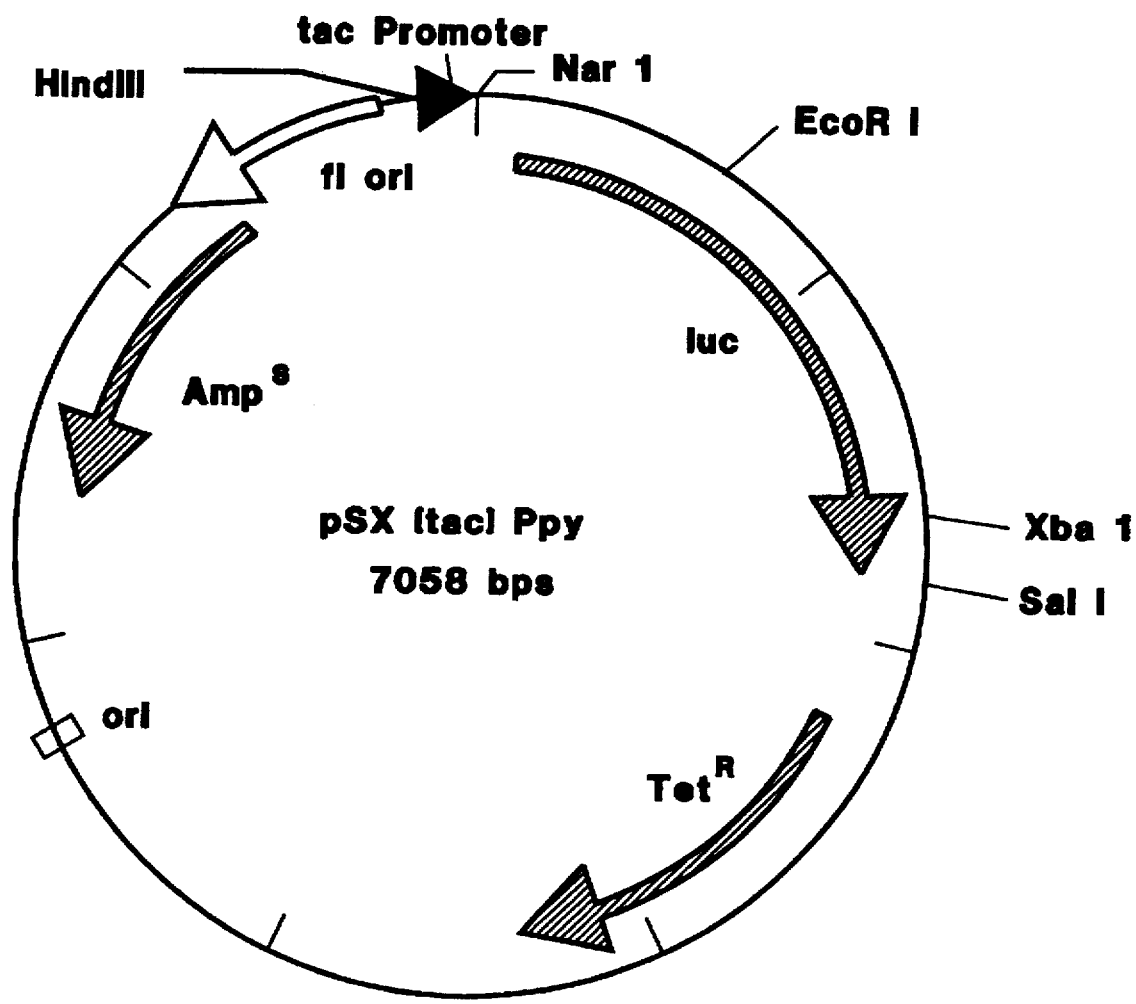
FIG. 3 shows a genetic map of a recombinant plasmid pSx tac) Ppy.

Plasmid pGL2X (FIG. 2) was constructed by introducing an Xba I restriction site at the immediate 3' end of the luc cDNA contained within the eucaryotic expression plasmid pGL2-Control (FIG. 1) (Promega Corp., Madison, Wis.). This was accomplished by first subcloning the 2.3 Kb DNA fragment generated by EcoR I/Sal I restriction of pGL2-Control into complementary sites of the prokaryotic luciferase expression vector pSx(tac) Ppy (FIG. 3), performing site-directed mutagenesis to create the desired Xba I site, and then recloning the mutated EcoR I/Sal I restriction fragment back into the original pGL2-Control vector backbone. Plasmid pGL2X was constructed to accept all subsequent mutational variations of the luc gene, and to express the modified luciferase enzymes in transfected mammalian cells.

The luc cDNA contained in pSx(tac) Ppy was mutated to disrupt both an Xba I beginning at bp 48 and a 22 bp imperfect palindrome centered at the Xba I site. The mutated luciferase gene is designated luc:dX. Plasmid pSx(tac) Ppy containing luc:dX provided the target for all subsequent mutagenic reactions directed downstream of the internal Nar I site, thus allowing for the generation of cumulative mutations within the luciferase gene. Intermediate forms of luciferase mutants contained in pSx(tac) Ppy were easily transferred into plasmid pGL2X for expression analysis in mammalian cells by complementary subcloning of the 1.6 Kb luciferase DNA generated by Nar I/Xba I digestion.

Two independent strategies were used to remove the peroxisomal targeting sequence from luciferase. One strategy relied on random mutagenesis to randomly alter the last three amino acids of luciferase, followed by screening for clones exhibiting efficient luminescence. The other strategy relied on deliberate design to achieve a preconceived sequence known to be ineffective for peroxisomal targeting. The result of these two approaches was two structurally distinct protein termini (both by amino acid identities and by position within the three dimensional structure of the protein) which are related only by their lack of targeting activity.

(luc:dX+GKT). DNA and amino acid changes specific to the major internal palindrome site and C-terminus of these three pGL2 derivatives and pGL2X(luc+) are displayed in Table 1. In addition to the changes described in Table 1, pGL2X (luc+) embodies all DNA and amino acid changes listed in Table 2. The nucleotide sequence of luc+ and the amino acid sequence of the encoded luciferase are shown in Sequence Listings SEQ ID: No. 3 and SEQ ID: No. 4, respectively.

TABLE 1

| Plasmid | luc Palindrome Region | C-Terminal Sequence | Luciferase Localization |
|---|---|---|---|
| pGL2 | Ala Pro Phe Tyr Pro Leu Glu Asp Gly Thr Ala<br>GCG CCA TTCTAT CCT CTIA GAG GATGGA ACC GCT<br>#34              Xba I | Gly Lys Ser Lys Leu Stop<br>GGA AAG TCC AAA TTG TAA AAT<br>#1,636 | Peroxisomes |
| pGL2x | Ala Pro Phe Tyr Pro Leu Glu Asp Gly Thr Ala<br>GCG CCA TTCTAT CCT CTIA GAG GATGGA ACC GCT<br>#34              Xba I | Gly Lys Ser Lys Leu Stop<br>GGA AAG TCC AAA TTC TAG AAT<br>#1,636         Xba I | N/A |
| pGL2X (luc:dX) | Ala Pro Phe Tyr Pro Leu Glu Asp Gly Thr Ala<br>GCG CCA TTC TAT CCG CTG GAA GAT GGA ACC GCT<br>#34 | Gly Lys Ser Lys Leu Stop<br>GGA AAG TCC AAA TTG TAA TTC TAG AAT<br>#1,636         Xba I | Peroxisomes |
| pGL2X (luc:dX+GKT) | Ala Pro Phe Tyr Pro Leu Glu Asp Gly Thr Ala<br>GCG CCA TTC TAT CCG CTG GAA GAT GGA ACC GCT<br>#34 | Gly Lys Thr Stop<br>GGA AAG AAC TAA TTC TAG AAT<br>#1,636         Xba I | Cytosol |
| pGL2X (luc:dX+IAV) | Ala Pro Phe Tyr Pro Leu Glu Asp Gly Thr Ala<br>GCG CCA TTC TAT CCG CTG GAA GAT GGA ACC GCT<br>#34 | Gly Lys Ile Ala Val Stop<br>GGA AAG ATC GCC GTG TAA TTC TAG AAT<br>#1,636         Xba I | Cytosol |
| pGL2X (luc+) | Ala Pro Phe Tyr Pro Leu Glu Asp Gly Thr Ala<br>GCG CCA TTC TAT CCG CTG GAA GAT GGA ACC GCT<br>#34 | Gly Lys Ile Ala Val Stop<br>GGA AAG ATC GCC GTG TAA TTC TAG AAT<br>#1,636         Xba I | Cytosol |

Random Mutagenesis: In the strategy using random mutagenesis, an oligonucleotide was generated to randomly alter the DNA sequence encoding the peroxisome targeting sequence, Ser-Lys-Leu, at the C-terminus of luciferase. pSx(tac) Ppy DNA containing the population of random C-terminal mutations was used to transform *E. coli* JM109 cells. Ampicillin resistant colonies were screen for bright in vivo luminescence according to the method of Wood, et al. (1987). C-terminal DNA sequences of clones selected for high level luciferase expression were further analyzed for amino acid sequence deviation from the natural peroxisome targeting sequence. A mutant luciferase containing the C-terminal tripeptide Ile-Ala-Val was selected by this method and, combined with the modification to remove the palindrome, was designated luc:dX+IAV.

Designed Mutagenesis: An independent strategy employing sequence-specific mutagenesis was used to generate a second luciferase variant containing the sequence Gly-Lys-Thr in substitution of the natural peroxisome targeting sequence. This luciferase variant, combined with the modification to remove the palindrome, was designated luc:dX+GKT. The tripeptide Gly-Lys-Thr was generated by rational design based on investigation by Sommer, et al., (1992) on the affect of C-terminal amino acid composition on the import of luciferase into glycosomes of *Trypanosoma brucei*. Glycosomes are membrane bound organelles specialized for energy production through glycolytic processes. Thus, glycosomes are functionally different from peroxisomes. However, the signals directing intracellular trafficking of proteins to glycosomes are similar to, though seemingly less stringent than, signals that mediate the targeting of proteins to peroxisomes. The luc:dX+IAV and luc:dX+GKT variants were cloned into the Nar I/Xba I sites of pGL2X to generate plasmids pGL2X(luc:dX+IAV) and pGL2X (luc:dX+GKT). DNA and amino acid changes specific to the major internal palindrome site and C-terminus of these three pGL2 derivatives and pGL2X(luc+) are displayed in Table 1. In addition to the changes described in Table 1, pGL2X (luc+) embodies all DNA and amino acid changes listed in Table 2. The nucleotide sequence of luc+ and the amino acid sequence of the encoded luciferase are shown in Sequence Listings SEQ ID: No. 3 and SEQ ID: No. 4, respectively.

Other modifications: In addition to removing the peroxisomal translocation signal, several other modifications were made to enhance the reliability and convenience of luciferase as a genetic reporter. These modifications were made using the same methods as described above for the sequence specific downstream of the internal Nar I site.

Table 2 (below) presents the complete list of sequence modifications embodied in luc+, which can be divided into the following classes:

1. Restriction endonuclease sites. The native luciferase gene contains restriction sites for Xba I, EcoR I, BstE II, EcoR V, and Cla I. To facilitate subcloning of the gene into diverse genetic constructs, these sites were removed by changing nucleotides in the DNA sequence without affecting the amino acid sequence.

An Nco I site was added at the initiating methionine codon (ATG) to aid in subcloning into many vectors which contain this site. The Nco I site may also be used to create N-terminal fusion proteins with luciferase. However, for this purpose using luc+NF (see below) is recommended.

To generate the Nco I site, the same site-specific mutagenesis methods described above were used. The 0.62 Kb Hind III/EcoR I fragment of pGL2-Control Vector was subcloned into the pSx(tac) Ppy linearized with Hind III and EcoR I. Following mutagenesis, the mutated Hind III/EcoR I fragment was subcloned into pGL2X(luc:dX+IAV).

2. Regulatory sequences. Any reporter gene may contain regulatory sequences embedded within its coding region which could mediate genetic activity either through the gene's native regulatory function or as a consequence of spurious recognition by transcription factors in a foreign host. In either case, these sequences would interfere with the "genetically neutral" behavior expected of a reporter gene.

To minimize this possibility, the luciferase gene sequence was scanned using a database of consensus sequences for transcription factor binding sites (Faisst and Meyer, 1992).

Many sites which could potentially interact with common factors were removed. In some cases where it was convenient in the modification strategy, less common potential regulatory sites were also removed. As with the removal of restriction sites, the potential regulatory sites were removed through changes in the DNA sequence that do not affect the encoded amino acid sequence.

3. Removal of extended palindrome sequences in the luciferase gene. Three palindromic sequences which could spuriously affect expression (22bp, 18bp, and 16bp, each with one mismatch) were also removed. The physiological significance of these sequences is unknown, however, they present potential regions of mRNA secondary structure which can affect translational efficiency. Disrupting these palindrome sequences increased reporter signal strength. This modification affects the structure of the gene only, not the amino acid strength.

4. Codon usage—Conversion of rare codons to more common forms. In general, codon usage presumably reflects the availability of tRNA isoforms in different organisms. Efficiently expressed genes utilize the most abundant tRNA isoforms. Codon usage in mammalian cells reveals a preference for cytosine (C) or guanine (G) in the third codon position; many codons containing adenine (A) or thymidine (T) occur rarely.

However, beetle luciferases generally have a high A/T content, biasing the codon frequency significantly from that of mammals. To achieve a codon usage in the firefly luciferase gene that is more congruent with mammalian genetics, the sequence modifications described above were designed wherever possible to yield more common codons (Wada, K. et al., 1992).

Also, where possible in the modifications strategy, the codons were changed from ATA to ATC (Ile), GTA to GTG (Val), and TTA to CTG or CTC (Leu). These changes were chosen because they convert particularly infrequent codons to ones which are highly frequent. In total, of the 69 codons that were modified to create luc+, 54 represent more common codons in mammalian cells. The average usage frequency of all modified codons increases from 14.5 in luc to 25.7 in luc+ (usage frequency is the occurrence per 1000 codons).

5. Glycosylation sites. Native luciferase expressed in the peroxisomes or the cytosol normally does not contain any post-translational modifications. However, gene fusions may be made of luc+ (or luc+NF) which are intended to direct a hybrid protein into the endoplasmic reticulum or Golgi apparatus. In these cellular compartments, N-linked glycosylation is known to occur at -Asn-X-(Ser/Thr)—sequences, which would have an unknown effect on luciferase enzymatic activity. To prevent the potential occurrence of N-linked glycosylation, two consensus glycosylation sites within the luciferase sequence were altered. The modified enzyme does not exhibit any apparent change to its chemical activity. A third consensus glycosylation site is highly conserved among beetle luciferases and could not be altered in firefly luciferase without affecting enzyme performance. Most likely this site is not near the protein surface, possibly making it inaccessible for glycosylation.

6. Combining modifications that increase reporter signal strength into a common enzyme and gene. The modifications leading to greater reporter signal strength described above act through largely independent mechanisms, and thus their effects should be cumulative. Reporter signal strength is increased by combining the above described modifications into a common enzyme and associated gene structure to gain a cumulative enhancement.

TABLE 2

Summary of Luciferase Gene Modifications in luc+

| Purpose of Modification | Sequence Modification in luc+ | |
|---|---|---|
| Introduce Nco I site for the construction of N-terminal fusions with luc+. | luc: | $Met_1$ $Glu_2$<br>AAA ATG GAA |
| | luc+: | $Met_1$ $Glu_2$<br>TCC ATG GAA<br>Nco I |
| Remove internal Xba I site; disrupt extended palindrome. | luc: | #47  Xba I<br>CTCTAGAGG |
| | luc+: | CGCTGGAAG |
| Eliminate potential glycosylation and ATF sites. | luc: | $Asn_{50}$ $Ile_{51}$ $Thr_{52}$<br>AAC ATC ACG TACGCGGAA |
| | luc+: | $Asp_{50}$ $Ile_{51}$ $Thr_{52}$<br>GAC ATC ACT TACGCTGAG |
| Eliminate potential glycosylation site. | luc: | $Asn_{119}$ $Ile_{120}$ $Ser_{121}$<br>AAC ATT TCG |
| | luc+: | $Gly_{119}$ $Ile_{120}$ $Ser_{121}$<br>GGC ATT TCG |
| Remove potential TGT-3 site; improve codon usage. | luc: | #373<br>GTAGTGTTTGTT |
| | luc+: | GTGGTGTTCGTT |
| Improve codon usage. | luc: | #426<br>ATTACCAATAATCCAG |
| | luc+: | GCTCCCAATCATCCAA |
| Improve codon usage. | luc: | #546<br>ACCAGAGTCCTTTGATCGTGACAAA |
| | luc+: | GCCAGAGTCCTTCGATAGGGACAAG |
| Remove internal EcoR I site, improve codon usage. | luc: | #583  EcoR I<br>ATAATGAATTCC |
| | luc+: | ATCATGAACTCC |

TABLE 2-continued

Summary of Luciferase Gene Modifications in luc+

| Purpose of Modification | | Sequence Modification in luc+ |
|---|---|---|
| | | #608    BstE II |
| Remove internal BstE II site and potential AP2 and LF-A1 sites; improve codon usage. | luc:<br>luc+: | GGTTACCTAAGGGTGTGGCCCTTCCG<br>GTCTGCCTAAAGGTGTCGCTCTGCCT |
| | | #646 |
| Remove potential AP1 site. | luc:<br>luc+: | TGCGTCAG<br>TGCGTGAG |
| | | #820 |
| Improve codon usage. | luc:<br>luc+: | TTACGATCCCTTCAGGATTACAAA<br>CTGAGGAGCCTTCAGGATTACAAG |
| | | #856 |
| Improve codon usage. | luc:<br>luc+: | TTGCTAGTACCAACCCTATTTTCA<br>CTGCTGGTGCCAACCCTATTCTCC |
| | | #945 |
| Eliminate internal palindrome; improve codon usage. | luc:<br>luc+: | GGGCGCACCTCTTTCGAAA<br>TGGCGCTCCCCTCTCTAAG |
| | | #984 |
| Improve codon usage. | luc:<br>luc+: | AAAACGCTTCCATCTTCCAGGGATACGA<br>CAAGAGGTTCCATCTGCCAGGTATCAGG |
| | | #1158 |
| Eliminate potential AP1 site; improve codon usage. | luc:<br>luc+: | GAGAGGCGAATTATGTGTCAGAGGA<br>AAGAGGCGAACTGTGTGTGAGAGGT |
| | | #1302 |
| Eliminate palindrome structure; improve codon usage. | luc:<br>luc+: | AGTTGACCGCTTGAAGTCTTTAATTAAATAC<br>CGTTGACCGCCTGAAGTCTCTGATTAAGTAC |
| | | #1333   EcoR V |
| Remove internal EcoR V site; improve codon usage. | luc:<br>luc+: | AAAGGATATCAGGTGGCC<br>AAAGGCTATCAGGTGGCT |
| | | #1365  Cla I |
| Remove internal Cla I site; improve codon usage. | luc:<br>luc+: | ATCGATATTGTTA<br>ATCCATCTTGCTC |
| | | #1400 |
| Remove potential Sp1 and AP2 sites. | luc:<br>luc+: | CGGGCGTGGC<br>CAGGTGTCGC |
| Remove peroxisome targeting sequence. | luc:<br>luc+: | $Gly_{546}$ $Lys_{547}$ $Ser_{548}$ $Lys_{549}$ $Leu_{550}$ stop<br>GGA AAG TCC AAA TTG TAA<br>$Gly_{546}$ $Lys_{547}$ $Ile_{548}$ $Ala_{549}$ $Val_{550}$ stop<br>GGA AAG ATC GCC GTG TAA |

The numbering scheme for amino acids is relative to the first amino acid, Met #1, of luciferase. The numbering of nucleotides is relative to the first base, "A", of the luciferase open reading frame.

N-terminal fusions with luciferase: luc+NF:

A variation of luc+, designated luc+NF, was designed for easier construction of N-terminal fusions (NF) with luciferase. The nucleotide sequence of luc+NF and the amino acid sequence of the encoded luciferase are shown in the Sequence Listings SEQ ID: No. 5 and SEQ ID: No. 6, respectively.

The luc+NF gene contains a unique BstE II restriction site located immediately downstream of the luciferase translational initiation codon (ATG). This site was generated by the same site-specific mutagenesis methods described above, yielding the sequence CC ATG GTC ACC GAC GCC from AA ATG GAA GAC GCC. The necessary manipulations to modify upstream of the Nar I site were the same as described above for generating luc+. Following mutagenesis, the Hind III/EcoR I fragment was subcloned into pGL2X(luc:dX+IAV) to yield pGL2X(luc:KNB+dX+IAV).

The BstE II site allows construction of N-terminal fusions that replace the original ATG codon by the newly introduced DNA; sequences also may be placed between the luciferase gene and its initiation codon. By removing the ATG codon from the fusion site, spurious internal initiation at this codon can be confidently avoided, preventing the possibility of coexpressing full-length, unfused luciferase. Internal initiation from the next available ATG codon generates a polypeptide which is too short to support luminescence.

Concomitant with placement of the BstE II site in luc+NF is the generation of two new amino acids at positions 2 and 3 of the modified luciferase enzyme. The altered N-terminal amino acid sequence of luc+NF, illustrated in Sequence Listing SEQ ID: No. 6, reduces luciferase expression 4 to 5-fold relative to that produced by the luc+ construct. Therefore, luc+NF is recommended specifically for the construction of N-terminal fusion proteins devoid of an internal ATG codon at the luciferase juncture, or that require the resident ATG for translational initiation.

New cassette vectors: pSP-luc+ and pSP-luc+NF:

pSP-luc+ and pSP-luc+NF are cassette plasmids containing the improved firefly luciferase genes, luc+ and luc+NF. These cassette vectors are not themselves intended for the eukaryotic expression of luciferase because they do not contain eukaryotic genetic regulatory elements. The luc+ and luc+NF gene are positioned downstream of an SP6 promoter and minimal ribosome binding site which, in the presence of SP6 polymerase, drive in vivo and in vitro expression of the modified luciferases. An opposing T7 promoter is also located immediately downstream of luc+ and luc+NF. These promoters allow for the convenient synthesis of sense and anti-sense luc+ or luc+NF transcripts for studies involving in situ hybridization, RNA processing, RNA transfection, or coupled in vitro transcription/translation and protein folding. Multiple cloning sites containing recognition sequences for a number of commonly used restriction enzymes are positioned 5' and 3' of luc+ and luc+NF.

EXAMPLES

The following examples are presented to illustrate the advantages of the present invention and to assist one of ordinary skill in making and using the same. The examples are not intended in any way to otherwise limit the scope of the disclosure or protection granted by the patent.

A major concern in the use of the native firefly luciferase as a genetic reporter is its intracellular partitioning into peroxisomes. The presence of this foreign protein in peroxisomes, and moreover, the resulting competition with native host proteins for peroxisomal transport has undefined affects on the normal cellular physiology. Variable subcellular localization of luciferase also compromises its value as a quantitative marker of gene activity. These potential problems reduce the general reliability of luciferase in reporter applications.

In the present invention, modified forms of luciferase were created which have the peroxisomal targeting sequence removed, or otherwise inactivated. The specific structural changes of these modifications are shown in Table 2. Expression of these modified luciferases in eukaryotic cells yields greater luminescence. Since the increased expression is evident for luciferases containing structurally independent modifications, the improved reporter activity is due to the inactivation of the peroxisomal targeting sequence and not to structural nuances of the modifications. Other modification of the luciferases revealed that eliminating a palindrome sequence from the encoding gene also yielded greater expression of the reporter.

Example 1

Expression of Modified Luciferases in Mammalian Cells

Plasmids expressing the non-mutated luc cDNA and three mutant variations were introduced into NIH3T3 cells to determine relative luciferase activities present in their prepared cell extracts. The plasmids tested were i) pGL2-Control containing the non-mutated luc gene, ii) pGL2X (luc:dX) expressing luc mutated to disrupt the major palindrome sequence centered between base pair 51 and 52, iii) pGL2X(luc:dX+IAV) containing luc mutated to disrupt the major palindrome sequence and to substitute the native Ser-Lys-Leu C-terminal tripeptide for Ile-Ala-Val and iv), pGL2X(luc:dX+GKT) containing luc mutated to disrupt the major palindrome sequence and to substitute the native C-terminal tripeptide for Gly-Lys-Thr.

Plasmid DNA's were delivered into cultured mammalian cells using a modified calcium phosphate-mediated transfection procedure. NIH3T3 cells were cultured in 75 cm$^2$ polystyrene culture flasks containing 25 ml of DMEM+FCS medium (Dulbecco's Modified Eagles Medium supplemented with 10% calf serum). Culture flasks containing cells were incubated in a 37° C./5% CO$_2$ environment until approximately 80% confluence was observed. Growth medium was removed and the cell monolayer was covered with 5 ml of Trypsin-EDTA solution diluted ten-fold with Hank's Balanced Salts solution. The trypsin solution was aspirated 30 seconds after addition and cells were allowed to incubate for 2 minutes at 37° C. Cells were harvested by rinsing the culture flask with of 10 ml of medium. Cell titer was determined and 3.0×10$^6$ cells were transferred to a 50 ml, sterile, screw-cap tube containing sufficient medium to obtain a final cell suspension volume of 33 ml.

In separate preparations, 1.8 ml of 250 mM CaCl$_2$ containing 15 µg of plasmid pCAT-Control (Promega Corp., Madison, Wis.) and 30 µg of either plasmid pGL2-Control, plasmid pGL2X(luc:dX), plasmid pGL2X(luc:dX+IAV), or plasmid pGL2X(luc:dX+GKT) were added to 1.8 ml of 2× HEPES buffer. The resulting 3.6 ml volumes of colloidal DNA/calcium phosphate were added to the prepared 33 ml volumes of cell suspension. The combined suspensions were rapidly mixed and 12 ml aliquots were immediately dispensed into each of three 100 cm$^2$ round polystyrene culture plates. Each plate contained the equivalent of 1×10$^6$ cells, 5 µg of control plasmid encoding CAT and 10 µg of an experimental plasmid encoding a luciferase variant. Transfected cells were incubated in a 37° C./5% CO$_2$ environment for 20 hr prior to providing the cells with fresh medium.

At 30 hours post-transfection each culture was harvested by removing growth medium, washing the adherent cells once with 10 ml phosphate buffered saline (PBS; 137 mM NaCl, 2.68 mM KCl, 1.47 mM KH$_2$PO$_4$, 8.1 mM Na$_2$HPO$_4$; pH 7.4), adding 1 ml Reporter Lysis Buffer (RLB) and scraping vigorously with a plastic cell lifter. Lysates were transferred to 1.5 ml microfuge tubes and cleared of cellular debris by spinning at 14,000 rpm in a refrigerated microfuge. Luciferase activities and chloramphenicol acetyl transferase (CAT) activities were quantified as described in Promega's Technical Bulletins #101 and #084, respectively (Promega Corporation, Madison, Wis.). CAT activities determined for individual cultures within a given experimental set were used as internal standards, and provided a means of normalizing the determined experimental luciferase activities.

All cell culture grade medium components, Trypsin-EDTA and salt solutions were obtained from GibcoBRL (Gaithersburg, Md.). All plastic ware was obtained from Corning (Corning, N.Y.). CaCl$_2$, and HEPES buffer solutions are components of the Profection® Mammalian Transfection System available from Promega Corp. (Madison, Wis.). RLB and all luciferase and CAT assay reagents and protocols are provided as components of the Luciferase Assay System and CAT Enzyme Assay System kits available from Promega Corp. (Madison, Wis.).

Figure 4:
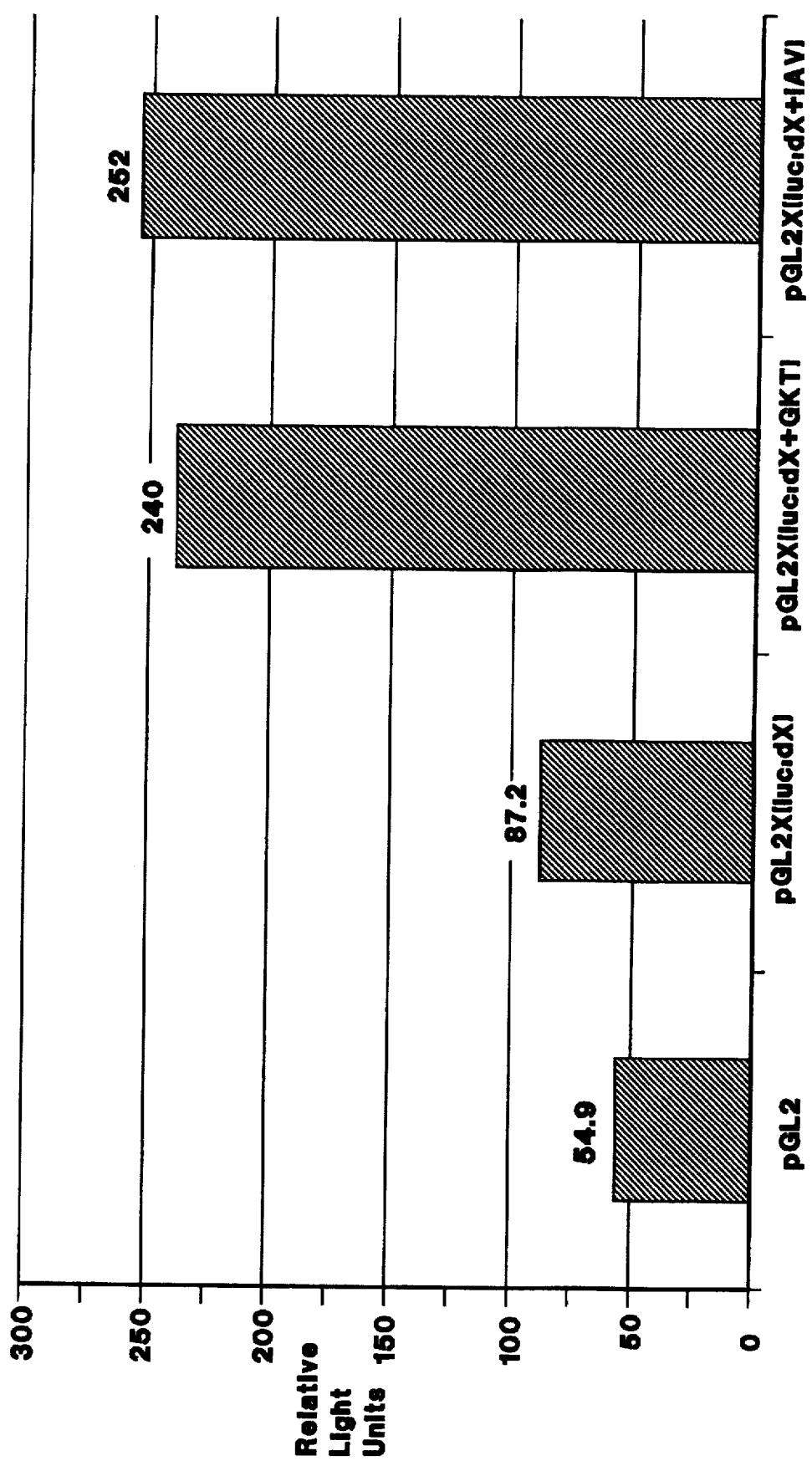
FIG. 4 is a chart illustrating the results of Example 1.

The results of these experiments, shown in FIG. 4, reveal that targeting into peroxisomes suppresses luciferase expression. This suppression limits reporter sensitivity and demonstrates modulation of reporter activity by a means other than gene transcription. By removing the effect of peroxisomal targeting, greater expression is achieved and reporter activity is disassociated from peroxisome physiology. This is especially important since prior results show that luciferase often is partitioned into both peroxisomes and the cytosol due to saturation of the translocation mechanism. Changes in expression would alter the balance of this partition, thus modulating the reporter activity. By inactivating the peroxisomal target sequence, the effects of partitioning are eliminated.

The results also reveal that a palindrome in the luciferase gene suppresses expression. By disrupting this palindrome through mutagenesis without altering the encoding of amino acid, greater luciferase expression was achieved.

Example 2

In vivo Measurement of Modified Luciferases in Mammalian Cells

Expression of luciferase may also be measured from living cells by adding the substrate luciferin to the growth medium. Luminescence is thus emitted from the cells without disrupting their physiology. Experimental results show that the modified luciferase gene yields greater luminescence expression also when measured from living cells.

The level of in vivo luciferase expression was compared between NIH3T3 cells transfected with plasmid pGL2-Control expressing luc cDNA, or plasmid pGL2X(luc:dX+IAV) expressing luc mutated to disrupt the major palindrome sequence and to substitute the Ser-Lys-Leu peroxisome targeting tripeptide with Ile-Ala-Val. Transfection and preparation of NIH3T3 cells were performed as described in Example 1, except that plasmid pCAT-Control was not included. As described, the 3.6 ml volumes of prepared colloidal DNA/calcium phosphate were added directly to the prepared 33 ml volumes of cell suspension and rapidly mixed. 3 ml aliquots were immediately dispensed into each of twelve pre-sterilized, flat-bottom, 28 mm O.D. borosilicate vials containing threaded caps (Fisher Scientific, Pittsburgh, Pa.).

The culture vials, each containing the equivalent of $2.5 \times 10^5$ cells and 2.5 µg of plasmid DNA, were incubated in a 37° C./5% $CO_2$ environment for 20 hr prior to providing the culture with 1 ml of fresh medium. At 30 hours post-transfection each culture medium was supplemented with an additional 1 ml of 37° C. medium containing 1.0 mM luciferin, 1% DMSO, and 0.01% Tween-20. In vivo expression of the luciferase reporter gene was determined by placing individual culture vials in the sample chamber of a Turner Designs Model 20e Luminometer (Turner Designs, Sunnyvale, Calif.) and quantifying cellular light emission every 15 seconds over a 3.25 minute period.

Figure 5:
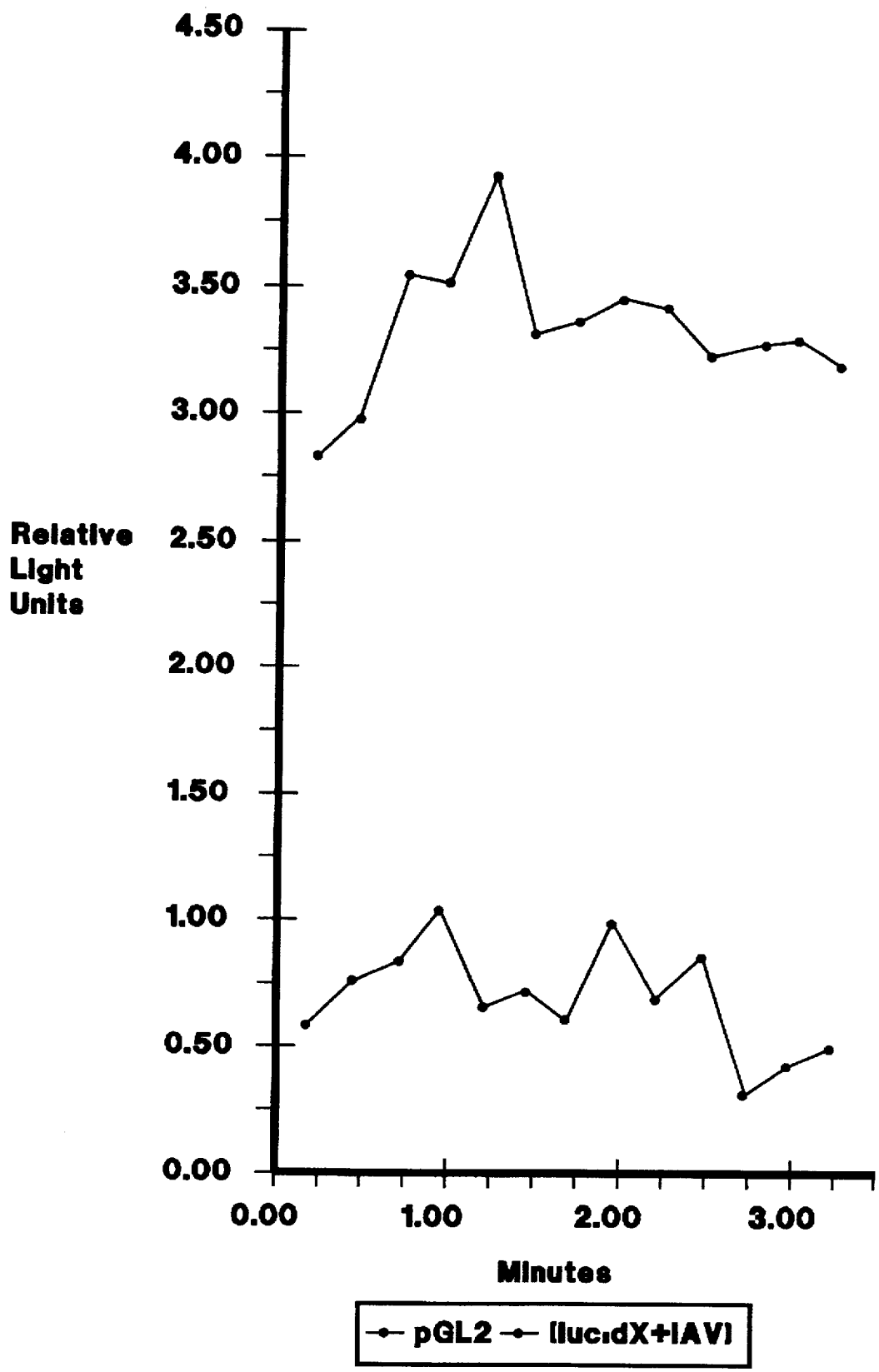
FIG. 5 is a chart illustrating the enhanced in vivo luminescence resulting from the changes in the plasmid pGL2X (luc:dX+IAV) in Example 2.

Reference is made to FIG. 5, which illustrates enhanced in vivo luminescence resulting from the changes embodied in the plasmid pGL2X(luc:dX+IAV).

Example 3

Expression of Modified Luciferases with N-Terminal Fusion Site in Mammalian Cells Constructs of fused genes that contain an ATG codon at the fusion juncture frequently suffer from some level of internal (i.e., spurious) translational initiation. This phenomenon causes a persistent low-level co-expression of the unfused reporter protein that cannot be easily discriminated from the expression pattern of the desired fusion construct. It is not uncommon to find that the enzymatic activity of a reporter enzyme is diminished by adding to it a fusion partner. Therefore, co-expression of a chimeric reporter enzyme and the natural reporter enzyme will undermine accurate and meaningful interpretation of any experimental results in which enzymatic activity of the fused protein is intended to report in vivo physiological responses.

The Nco I restriction site at the N-terminus of luc+ allows only for the construction N-terminal luciferase fusions which retaining the resident luciferase initiation codon at the fusion juncture. To extend the utility of luc+ in constructing N-terminal fusions, the gene was modified to include a unique BstE II restriction site beginning at nucleotide 2 of the luciferase gene. This gene variation, designated luc+NF, enables the construction of N-terminal fusions in which the resident ATG (Met) of luciferase is either excluded or segregated to the new N-terminus of the fusion protein.

An intermediate in the design of luc+ is luc:KNB+dX+IAV which contains only the modified N-terminal sequence, the disrupted 22 bp palindrome, and the modified C-terminus encoding Ile-Ala-Val. This intermediate was made by the methods described above. Comparative in vitro analysis of expression levels were conducted using NIH3T3 cells transfected with plasmids pGL2-Control, pGL2X (luc:KNB+dX+IAV) and pGL2X(luc:dX+IAV). Expression of luciferase from luc:KNB+dX+IAV is greater than that of the unmodified peroxisomal luciferase encoded by luc. Because the modified N-terminus alone is known to reduce expression efficiency 4 to 5-fold, the increase in expression evident in this experiment is due to elimination of peroxisomal targeting.

Figure 6:
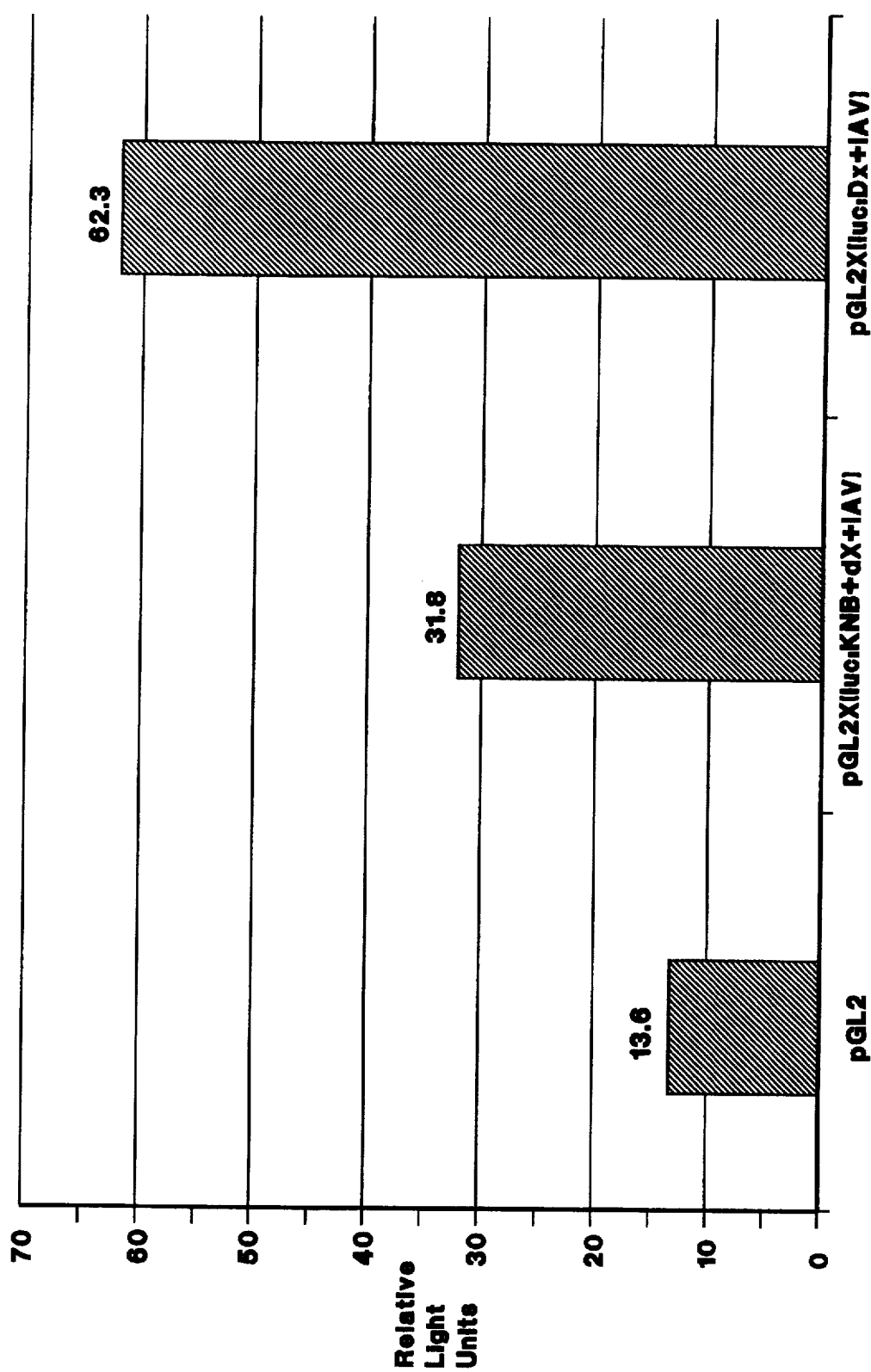
FIG. 6 is a chart illustrating the enhanced luminescence of plasmid pGL2X(luc:KNB+dX+IAV) over unmodified luciferase in Example 3.

FIG. 6 demonstrates that the plasmid pGL2X(luc:KNB+dX+IAV) shows enhanced luminescence over the unmodified, i.e., peroxisomal, luciferase (pGL2).

Example 4

Difference Between luc+ and luc in NIH3T3 Cells, HeLa Cells, CHO Cells and CV-1 Cells Performance of luc+ in mammalian cells The changes incorporated into luc+ are intended to minimize the potential for unexpected interferences with reporter performance under specific experimental conditions, providing a more reliable indicator of genetic activity than the native luciferase cDNA clone. The specific changes to the structure of the luciferase gene are listed in Table 2, and include the modifications described in Examples 1 through 3. The structure of luc+NF is identical to luc+ except for a modification to the N-terminus allowing for optimal creation of gene fusions. The structures of luc+ and luc+NF represent the optimal compositions of the invention.

In other cell types, differences between the performance of luc+ and luc are apparent. To show this, four mammalian cell lines, NIH3T3, HeLa, CHO, and CV-1, were tested for their level of expressing peroxisomal luciferase encoded by luc, and cytosolic luciferase encoded by luc+. Plasmid pGL2-Control, which expresses the unmodified peroxisomal luciferase enzyme, and plasmid pGL2X(luc+), which expresses the engineered cytosolic luciferase enzyme, were introduced into CHO, NIH3T3, CV-1 and HeLa cells. Cells were prepared and transfected using the calcium phosphate-mediated transfection procedure described in Example 1. Cells were cultured in 75 $cm^2$ polystyrene culture flasks containing 25 ml of either DMEM+FCS medium or DMEM/F12+FCS medium (a 50:50 combination of Dulbecco's Modified Eagles Medium and Ham F12 Nutrient Mix, further supplemented with 10% calf serum).

The results showed that in cell lines expressing relatively high levels of luciferase activity, the performance of luc+ and luc were comparable (Table 3). With the lower levels of expression, however, luc+ supported relatively higher levels of luciferase. From our earlier experiments in NIH3T3 cells, this greater level of expression is due predominantly to the removal of the peroxisomal translocation signal, suggesting the difference in luciferase expression here is apparently associated with its translocation into peroxisomes.

These results are consistent with the hypothesis that peroxisomal targeting suppresses reporter expression. Since higher levels of expression led to saturation of the peroxisomes, a large portion of the native luciferase synthesized in CHO and CV-1 cells may be in the cytosol. These conditions should minimize differences between the cytoplasmic form of luciferase encoded by luc+ and the native luciferase encoded by luc. Under lower levels of expression, however, the differences between the luciferase forms would become more apparent as they are increasingly segregated into their respective subcellular compartments.

TABLE 3

Relative Expression of luc+ and luc in Various Mammalian Cell Lines

| Cell Type | Relative Luminescence Expression | | Ratio |
|---|---|---|---|
| | luc | luc+ | |
| NIH3T3 | 0.0011 | 0.0050 | 4.7 |
| HeLa | 0.0033 | 0.0062 | 1.9 |
| CHO | 0.18 | 0.20 | 1.1 |
| CV-1 | 0.90 | 1.00 | 1.1 |

It is understood that the invention is not confined to the particular construction and arrangements herein illustrated and described, but embraces such modified forms thereof and come within the scope of the claims following the bibliography.

BIBLIOGRAPHY

Bronstein, et al. (1994) *Cal. Biochem.:* 219, 19–181.
Brachmair, et al. (1986) *Science:* 234, 179.
de Wet, et al. (1985) *PNAS:* 82, 7870.
de Wet, et al., 1987, *Molec. Cel Biol.:* 7, 725.
Faisst, S. and Meyer, S. (1992) *Nucleic Acid. Res.:* 20,
Gould, S. J. et al. (1990) *J. Cell Biol.* 110: 27.
Gould, S. J. et al. (1989) *J. Cell Biol.* 108: 1657.
Keller, G.-A. et al. (1987) *Cell Biol.* 84: 3264.
Lewis, M. K. and D. V. Thompson (1990) *Nuc. Acids Res.* 18: 3439–3443.
Sommer, J. M. et al. (1992) *Mol. Biol. Cell.* 3, 749.
Wada, K. et al. (1992) *Nucleic Acid Res.* 20, 2111.
Wood, K. V. and M. DeLuca (1987) *Anal. Biochem.* 161 501–507.
ProFection® Mammalian Transfection Systems Technical Bulletin #TM012, Promega Corporation.
Luciferase Assay Systems Technical Bulletin #TB101, Promega Corporation.

What is claimed is:

1. A luciferase gene encoding a modified form of the luciferase of *Photinus pyralis*, wherein:

a. the internal palindrome sequence beginning at nucleotide 40 of SEQ. ID. NO: 1 is eliminated by changing the DNA sequence beginning at nucleotide 40 of SEQ. ID. NO: 1 to the DNA sequence of SEQ. ID. NO: 7, namely, TTC TAT CCG CTG GAA GAT GGA A;

b. the near consensus TGT-3 regulatory site beginning at nucleotide 373 of SEQ. ID. NO: 1 is altered by changing the DNA sequence beginning at nucleotide 373 of SEQ. ID. NO: 1 to SEQ. ID. NO: 9, namely, GTG GTG TTC GTT, wherein such change in DNA sequence is conducted without affecting the amino acid sequence;

c. the near consensus AP1 regulatory site beginning at nucleotide 646 of SEQ. ID. NO: 1 is altered by changing the DNA sequence of SEQ. ID. NO: 1 at nucleotide 646 to SEQ. ID. NO: 11, namely, TGC CGT AG, wherein such change in DNA sequence is conducted without affecting the amino acid sequence;

d. the near consensus AP1 regulatory site beginning at nucleotide 1158 of SEQ. ID. NO: 1 is altered by changing the DNA sequence of SEQ. ID. NO: 1 at nucleotide 1158 to SEQ. ID. NO: 13, namely, AAG AGG CGA ACT GTG TGT GAG AGG T, wherein such change is conducted without affecting the amino acid sequence;

e. the near consensus AP1 and Sp1 regulatory sites beginning at nucleotide 1400 of SEQ. ID. NO: 1 are altered by changing the DNA sequence of SEQ. ID. NO: 1 at nucleotide 40 to SEQ. ID. NO: 15, namely, CAG GTG TCG C, wherein such change is conducted without affecting the amino acid sequence;

f. the glycosylation site beginning at amino acid 50 of SEQ. ID. NO: 2 is eliminated by replacing asparagine with aspartate;

g. the glycosylation site beginning at amino acid 50 of SEQ. ID. NO: 1 is eliminated by replacing the tripeptide codon sequence beginning at nucleotide 148 of SEQ. ID. NO: 1 with SEQ. ID. NO: 17, namely, GAC ATC ACT, such that the amino acid sequence asparagine-isoleucine-threonine is replaced with aspartate-isoleucine-threonine;

h. the glycosylation site beginning at amino acid 119 of SEQ. ID. NO: 2 is eliminated by replacing asparagine with glycine; and i. the glycosylation site beginning at amino acid 119 of SEQ. ID. NO: 1 is eliminated by replacing the tripeptide codon sequence beginning at nucleotide 355 of SEQ. ID. NO: 1 with SEQ. ID. NO. 19, namely, GGC ATT TCG, such that the amino acid sequence asparagine-isoleucine-serine is replaced with glycine-isoleucine-serine.

2. A recombinant DNA comprising the gene of claim 1.

3. A host cell containing the recombinant DNA of claim 2.

4. A modified luciferase gene having the nucleotide sequence illustrated in SEQ. ID. NO. 3.

5. A modified luciferase gene which encodes the amino acid sequence illustrated in SEQ. ID. NO. 4.

6. A luciferase gene encoding luciferase of *Photinus pyralis* comprising a DNA encoding functional luciferase wherein an Xba I restriction site beginning at nucleotide 48 of SEQ ID NO: 1 and a 22-base pair imperfect palindrome centered at the Xba I restriction site of SEQ ID NO: 1 are disrupted without affecting the amino acid sequence of the encoded luciferase.

7. The luciferase gene according to claim 6, wherein the DNA sequence at nucleotides 48 through 54 of SEQ ID NO: 1 is changed from T CTA GAG to G CTG GAA.

8. The luciferase gene according to claim 6, further comprising a DNA which encodes a functional luciferase gene product having a C-terminal amino acid sequence of glycine-lysine-threonine.

9. The luciferase gene according to claim 6, further comprising a DNA which encodes a functional luciferase gene product having a C-terminal amino acid sequence of isoleucine-alanine-valine.

10. A method of using a luciferase gene to eliminate peroxisomal influence on expression of a luciferase gene product in a heterologous eucaryotic host comprising:

stably or transiently incorporating a mutated luciferase gene which encodes a cytoplasmic form of a luciferase gene product into the heterologous eucaryotic host, whereby peroxisomal influence on the expression of the luciferase gene product is eliminated, the mutated luciferase gene selected from the group consisting of a DNA encoding functional luciferase wherein an Xba I restriction site beginning at nucleotide 48 of SEQ ID NO: 1 and a 22-base pair imperfect palindrome centered at the Xba I restriction site of SEQ ID NO: 1 are disrupted without affecting the amino acid sequence of the encoded luciferase, a DNA encoding functional luciferase wherein an Xba I restriction site beginning at nucleotide 48 of SEQ ID NO: 1 and a 22-base pair imperfect palindrome centered at the Xba I restriction site of SEQ ID NO: 1 are disrupted without affecting the amino acid sequence of the encoded luciferase and wherein the DNA encodes a gene product having a C-terminal amino acid sequence of glycine-lysine-threonine, and a DNA encoding functional luciferase wherein an Xba I restriction site beginning at nucleotide 48 of SEQ ID NO: 1 and a 22-base pair imperfect palindrome centered at the Xba I restriction site of SEQ ID NO: 1 are disrupted without affecting the amino acid sequence of the encoded luciferase and wherein the DNA encodes a gene product having a C-terminal amino acid sequence of isoleucine-alanine-valine.

11. The method according to claim 10, wherein the luciferase gene comprising a DNA encoding functional luciferase wherein an Xba I restriction site beginning at nucleotide 48 of SEQ ID NO: 1 and a 22-base pair imperfect palindrome centered at the Xba I restriction site of SEQ ID NO: 1 are disrupted without affecting the amino acid sequence of the encoded luciferase is stably or transiently incorporated into the heterologous eucaryotic host.

12. The method according to claim 10, wherein the luciferase gene comprising a DNA encoding functional luciferase wherein an Xba I restriction site beginning at nucleotide 48 of SEQ ID NO: 1 and a 22-base pair imperfect palindrome centered at the Xba I restriction site of SEQ ID NO: 1 are disrupted without affecting the amino acid sequence of the encoded luciferase and wherein the DNA encodes a gene product having a C-terminal amino acid sequence of glycine-lysine-threonine is stably or transiently incorporated into the heterologous eucaryotic host.

13. The method according to claim 10, wherein the luciferase gene comprising a DNA encoding functional luciferase wherein an Xba I restriction site beginning at nucleotide 48 of SEQ ID NO: 1 and a 22-base pair imperfect palindrome centered at the Xba I restriction site of SEQ ID NO: 1 are disrupted without affecting the amino acid sequence of the encoded luciferase and wherein the DNA encodes a gene product having a C-terminal amino acid sequence of isoleucine-alanine-valine is stably or transiently incorporated into the heterologous eucaryotic host.

14. A method of using a luciferase gene to increase total activity of a luciferase gene product in a heterologous eucaryotic host comprising:

stably or transiently incorporating a mutated luciferase gene which encodes a cytoplasmic form of a luciferase gene product into the heterologous eucaryotic host, whereby total activity of the luciferase gene product is increased, the mutated luciferase gene selected from the group consisting of a DNA encoding functional luciferase wherein an Xba I restriction site beginning at nucleotide 48 of SEQ ID NO: 1 and a 22-base pair imperfect palindrome centered at the Xba I restriction site of SEQ ID NO: 1 are disrupted without affecting the amino acid sequence of the encoded luciferase, a DNA encoding functional luciferase wherein an Xba I restriction site beginning at nucleotide 48 of SEQ ID NO: 1 and a 22-base pair imperfect palindrome centered at the Xba I restriction site of SEQ ID NO: 1 are disrupted without affecting the amino acid sequence of the encoded luciferase and wherein the DNA encodes a gene product having a C-terminal amino acid sequence of glycine-lysine-threonine, and a DNA encoding functional luciferase wherein an Xba I restriction site beginning at nucleotide 48 of SEQ ID NO: 1 and a 22-base pair imperfect palindrome centered at the Xba I restriction site of SEQ ID NO: 1 are disrupted without affecting the amino acid sequence of the encoded luciferase and wherein the DNA encodes a gene product having a C-terminal amino acid sequence of isoleucine-alanine-valine.

15. The method according to claim 14, wherein the luciferase gene comprising a DNA encoding functional luciferase wherein an Xba I restriction site beginning at nucleotide 48 of SEQ ID NO: 1 and a 22-base pair imperfect palindrome centered at the Xba I restriction site of SEQ ID NO: 1 are disrupted without affecting the amino acid sequence of the encoded luciferase is stably or transiently incorporated into the heterologous eucaryotic host.

16. The method according to claim 14, wherein the luciferase gene comprising a DNA encoding functional luciferase wherein an Xba I restriction site beginning at nucleotide 48 of SEQ ID NO: 1 and a 22-base pair imperfect palindrome centered at the Xba I restriction site of SEQ ID NO: 1 are disrupted without affecting the amino acid sequence of the encoded luciferase and wherein the DNA encodes a gene product having a C-terminal amino acid sequence of glycine-lysine-threonine is stably or transiently incorporated into the heterologous eucaryotic host.

17. The method according to claim 14, wherein the luciferase gene comprising a DNA encoding functional luciferase wherein an Xba I restriction site beginning at nucleotide 48 of SEQ ID NO: 1 and a 22-base pair imperfect palindrome centered at the Xba I restriction site of SEQ ID NO: 1 are disrupted without affecting the amino acid sequence of the encoded luciferase and wherein the DNA encodes a gene product having a C-terminal amino acid sequence of isoleucine-alanine-valine is stably or transiently incorporated into the heterologous eucaryotic host.

* * * * *